United States Patent
Rondoni et al.

(10) Patent No.: US 7,855,653 B2
(45) Date of Patent: Dec. 21, 2010

(54) EXTERNAL VOIDING SENSOR SYSTEM

(75) Inventors: John C. Rondoni, Plymouth, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 955 days.

(21) Appl. No.: 11/414,508

(22) Filed: Apr. 28, 2006

(65) Prior Publication Data

US 2007/0252713 A1 Nov. 1, 2007

(51) Int. Cl.
*G08B 23/00* (2006.01)
(52) U.S. Cl. ............... 340/573.5; 340/604; 340/539.12; 607/41; 604/361
(58) Field of Classification Search ............. 340/573.5, 340/539.12, 604; 607/40, 41; 604/361
See application file for complete search history.

(56) References Cited

U.S. PATENT DOCUMENTS

| | | |
|---|---|---|
| 3,530,855 A | 9/1970 | Balding |
| 3,759,246 A | 9/1973 | Flack et al. |
| 4,163,449 A | 8/1979 | Regal |
| 4,205,671 A | 6/1980 | Lassen |
| 4,760,383 A | 7/1988 | DiLorenzo |
| 4,873,990 A | 10/1989 | Holmes et al. |
| 4,928,690 A | 5/1990 | Heilman et al. |
| RE33,360 E | 10/1990 | Reynolds et al. |
| 4,977,906 A | 12/1990 | Di Scipio |
| 5,103,835 A | 4/1992 | Yamada et al. |
| 5,331,548 A | 7/1994 | Rollema et al. |
| 5,396,897 A | 3/1995 | Jain et al. |
| 5,423,329 A | 6/1995 | Ergas |
| 5,704,353 A | 1/1998 | Kalb et al. |
| 5,760,694 A | 6/1998 | Nissim et al. |
| 5,978,712 A | 11/1999 | Suda et al. |
| 6,051,017 A | 4/2000 | Loeb et al. |
| 6,289,245 B1 | 9/2001 | Mo et al. |
| 6,354,991 B1 | 3/2002 | Gross et al. |
| 6,360,123 B1 | 3/2002 | Kimichi et al. |
| 6,372,951 B1 * | 4/2002 | Ter-Ovanesyan et al. ..... 604/361 |

(Continued)

FOREIGN PATENT DOCUMENTS

FR 2 788 430 7/2000

(Continued)

OTHER PUBLICATIONS

"Notification Concerning Transmittal of Copy of International Preliminary Report on Patentability," dated Nov. 6, 2008 for corresponding PCT Application No. PCT/US2007/007834, (7 pgs.).

(Continued)

*Primary Examiner*—Jeffery Hofsass
(74) *Attorney, Agent, or Firm*—Shumaker & Sieffert, P.A.

(57) ABSTRACT

The disclosure describes an absorbent pad worn by a patient that measures one or more urinary voiding parameters. One or more sensors that measure voiding parameters are integrally formed with the pad, e.g., interwoven with the absorbent pad material or positioned to form one or more sensor layers between layers of absorbent material. The sensors store measured parameters as information in a memory, e.g., as a log, locally or in a separate device. In some embodiments, the pad includes an electrical stimulator that provides stimulation therapy for urinary incontinence based on measured parameters.

43 Claims, 15 Drawing Sheets

U.S. PATENT DOCUMENTS

| | | | |
|---|---|---|---|
| 6,384,728 | B1 | 5/2002 | Kanor et al. |
| 6,393,323 | B1 | 5/2002 | Sawan et al. |
| 6,433,695 | B1 | 8/2002 | Kai et al. |
| 6,454,720 | B1 | 9/2002 | Clerc et al. |
| 6,652,449 | B1 | 11/2003 | Gross et al. |
| 6,689,056 | B1 | 2/2004 | Kilcoyne et al. |
| 6,766,817 | B2 | 7/2004 | da Silva |
| 6,918,404 | B2 | 7/2005 | Dias da Silva |
| 6,941,171 | B2 | 9/2005 | Mann et al. |
| 7,066,586 | B2 | 6/2006 | da Silva |
| 7,203,548 | B2 | 4/2007 | Whitehurst et al. |
| 7,415,308 | B2 * | 8/2008 | Gerber et al. ............ 607/41 |
| 2002/0019615 | A1 | 2/2002 | Roe et al. |
| 2002/0055761 | A1 * | 5/2002 | Mann et al. ............ 607/41 |
| 2002/0062060 | A1 | 5/2002 | Gross et al. |
| 2002/0103424 | A1 | 8/2002 | Swoyer et al. |
| 2002/0111586 | A1 | 8/2002 | Mosel et al. |
| 2003/0060789 | A1 | 3/2003 | Shapira et al. |
| 2003/0100930 | A1 | 5/2003 | Cohen et al. |
| 2004/0147871 | A1 | 7/2004 | Burnett |
| 2004/0152999 | A1 | 8/2004 | Cohen et al. |
| 2004/0220538 | A1 | 11/2004 | Panopoulos |
| 2004/0230172 | A1 | 11/2004 | Shapira |
| 2005/0065408 | A1 | 3/2005 | Benderev |
| 2005/0099294 | A1 | 5/2005 | Bogner et al. |
| 2005/0113881 | A1 | 5/2005 | Gross et al. |
| 2005/0245840 | A1 | 11/2005 | Christopherson et al. |
| 2005/0288603 | A1 | 12/2005 | Goping |
| 2006/0004421 | A1 | 1/2006 | Bennett et al. |
| 2006/0020225 | A1 | 1/2006 | Gerber et al. |
| 2006/0247723 | A1 | 11/2006 | Gerber et al. |

FOREIGN PATENT DOCUMENTS

| | | |
|---|---|---|
| WO | WO 96/14813 | 5/1996 |
| WO | WO 01/00117 | 1/2001 |
| WO | WO 2004/049969 | 6/2004 |

OTHER PUBLICATIONS

Coosemans et al., "Datalogger for Bladder Pressure Monitoring with Wireless Power and Data Transmission," Katholieke Universiteit Leuven, Department ESAT-MICAS, Belgium, Belgian Day on Biomedical Engineering, 1 pg., 2003.

Siwapornsathain et al., "A Telemetry and Sensor Platform for Ambulatory Urodynamics," Department of Electrical and Computer Engineering, University of Wisconsin—Madison, 5 pgs., 2002.

"Wireless Physiological Pressure Transducer," Memscap Sensor Solutions, 2 pgs., May 2003.

"Standardisation of Ambulatory Urodynamic Monitoring," Report of the Standardisation sub-Committee of the ISC for Ambulatory Urodynamic Studies, 21 pgs. 2000.

Rondoni et al., "External Voiding Sensor System," U.S. Appl. No. 11/414,626, filed Apr. 28, 2006.

Office Action dated Apr. 30, 2008 for U.S. Appl. No. 11/414,626 (19 pgs.).

Responsive Amendment dated Jul. 30, 2008 for U.S. Appl. No. 11/414,626 (15 pgs.).

International Search Report and Written Opinion dated Aug. 6, 2007 for corresponding PCT Application No. PCT/US2007/007834, (11 pgs.).

European Examination Report dated Sep. 17, 2009 for corresponding Application No. 07754365.0 (5 pgs.).

Office Action dated Apr. 5, 2010 for U.S. Appl. No. 12/403,282 (24 pgs.).

Response to Office Action for U.S. Appl. No. 12/403,282, filed Jul. 6, 2010 (9 pgs.).

* cited by examiner

EXTERNAL VOIDING SENSOR SYSTEM

TECHNICAL FIELD

The invention relates to implantable medical devices and, more particularly, external sensors.

BACKGROUND

Urinary incontinence, or an inability to control urinary function, is a common problem afflicting people of all ages, genders, and races. Various muscles, nerves, organs and conduits within the urinary tract cooperate to collect, store and release urine. A variety of disorders may compromise urinary tract performance and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients also may suffer from nerve disorders that prevent proper triggering and operation of the bladder or sphincter muscles. Nerves running though the pelvic floor stimulate contractility in the sphincter. A breakdown in communication between the nervous system and the urinary sphincter can result in urinary incontinence.

Monitoring urinary incontinence aids a clinician in diagnosing the precise condition of the patient. For example, a clinician may monitor parameters, such as time of voiding events (voluntary and involuntary), volume of leaked fluid for an event, number of voiding events, and contents of urine, in order to diagnose the condition of the patient. Accordingly, monitoring may include collecting urine samples from the patient and/or maintaining a patient voiding diary in which the patient logs voluntary voiding events, involuntary voiding events, i.e., leakage, or other related problems. The patient may keep the voiding diary on paper or in an electronic device. The clinician may review the samples to determine the contents of the urine and may review the diary to view the frequency and number of voiding events experienced by the patient. In some cases, the clinician may tailor a therapy according to the diary and the contents of the urine samples.

Electrical stimulation of nerves in the pelvic floor may provide an effective therapy for a variety of disorders, including urinary incontinence. For example, an implantable electrical stimulator delivers electrical stimulation to the sacral nerve to induce sphincter constriction, and thereby close or maintain closure of the urethra at the bladder neck. In addition, electrical stimulation of the bladder wall may enhance pelvic floor muscle tone and assist fluid retention in the bladder or voiding fluid from the bladder. An appropriate course of neurostimulation therapy may be aided by the voiding diary.

SUMMARY

The disclosure is directed to an absorbent sensor pad worn by a patient that measures one or more urinary voiding parameters. One or more sensors that measure voiding parameters are integrally formed with the pad. For example, the sensors may be interwoven with the absorbent pad material or positioned to form one or more sensor layers between layers of absorbent material. The sensors store measured parameters as information in a memory, e.g., as a log, locally or in a separate device. In some embodiments, an electrical stimulator provides stimulation therapy for urinary incontinence based on parameters measured by the sensor pad.

Maintaining an accurate voiding diary is often difficult for a patient. The patient needs to spend time to manually enter a voiding event whenever it occurs and may neglect or forget to record all the necessary information. This manual diary also can be inaccurate because entries by the patient are subjective and may be influenced by embarrassment or other issues. In addition, a voiding diary is limited to information recorded by the patient such as voluntary voiding events, involuntary voiding events (leakage), time of voiding events, and other related problems.

It may be helpful to a clinician to monitor additional voiding parameters such as volume, contents, and temperature of urine voided by the patient as well as posture and activity of the patient during a voiding event. An absorbent wearable pad with integrally formed sensors that measure urinary voiding parameters, as described herein, may be beneficial in providing the patient with an objective sensing system that automatically measures voiding parameters and stores the information in a voiding log, without the need for significant patient interaction.

As described herein, the sensor pad includes one or more integrally formed sensors that measure urinary voiding parameters. The sensors may include various types of sensors such as impedance sensors, strain gauges, temperature sensors, accelerometers, pH sensors, and chemical sensors that measure wetness, volume, temperature, pH, and contents of urine voided by a patient as well as the posture and activity of the patient. The sensors may be positioned in a particular area of the pad, referred to as the sensor area.

In some embodiments, the sensor pad may be constructed to keep the patient substantially dry by directing voided urine away from the patient, e.g., allowing fluid to pass only through the depth of the pad. Accordingly, the sensor area may be strategically positioned in an area of the pad that is most likely to absorb urine voided by the patient. Within the sensor area, the sensors may be arranged in a two-dimensional sensor layer or a three-dimensional array. In some embodiments, the sensors may form an addressable sensor array that detects wetness by measuring a change in electrical resistance between electrodes in the array.

The sensors may be coupled to a master module, also integrally formed with the pad, that receives the measured parameters as input. The master module may include a processor that performs processing operations associated with the sensors and may include a memory for storing the voiding information. For example, the processor may detect a physiologic event, e.g., a voiding event, or determine the volume, contents, temperature, and pH of urine voided by the patient based on the input. The master module may transmit voiding information to an external device, via a wired or wireless connection, to display the voiding information, e.g., as a log, to the patient or clinician for review.

The pad may be constructed to support measurement of the parameters. For example, the pad may be constructed with a transport layer adjacent to the patient that transports fluid voided by the patient to a sensor area of the pad, a middle layer that includes the sensors and absorbent material, and a barrier layer that acts as a barrier to prevent fluid voided by the patient from leaking out of the pad. Within the second layer, the sensors may be interwoven with the absorbent material or one or more sensor layers may be separated by one or more absorbent layers. When the sensors are interwoven with the absorbent material, the pad may include more than one layer of absorbent material with interwoven sensors.

In some embodiments, a system according to an embodiment of the invention includes an electrical stimulator that delivers stimulation therapy to the patient for urinary incontinence. The sensor pad or an external device may automatically adjust the stimulation therapy after processing the voiding information. Alternatively, the user may manually adjust the stimulation parameters upon reviewing the voiding information.

In one embodiment, the invention is directed to a system comprising an absorbent pad for placement adjacent to a patient and one or more sensors integrally formed with the absorbent pad and positioned to measures one or more voiding parameters.

In another embodiment, the invention is directed to a method comprising sensing one or more voiding parameters via one or more sensors integrally formed within an absorbent pad disposed adjacent to a patient and storing the one or more voiding parameters in a voiding log as voiding information.

In various embodiments, the invention may provide one or more advantages. For example, the patient may discreetly wear an absorbable pad, e.g., as an undergarment or in combination with an undergarment, to automatically generate a voiding log based on measured parameters (voiding information) and detected events. This may allow the patient to eliminate the need to keep a manual voiding diary.

In addition, the pad may also automatically adjust stimulation parameters based on the measured parameters and detected events. In this manner, the pad may provide immediate adjustment to the therapy. Consequently, the pad may, for example, control a stimulator that stimulates a nerve or muscle of the patient to prevent the patient from unintentionally voiding his or her bladder in response to detecting wetness in the pad.

The undergarment may be disposable or washable to maintain a healthy detection environment. The system also allows the patient or clinician to review the voiding log and make changes to incorrect voiding information. The sensed information may also be used as feedback for manual or automatic adjustment of electrical stimulation therapy delivered to the patient for urinary incontinence.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
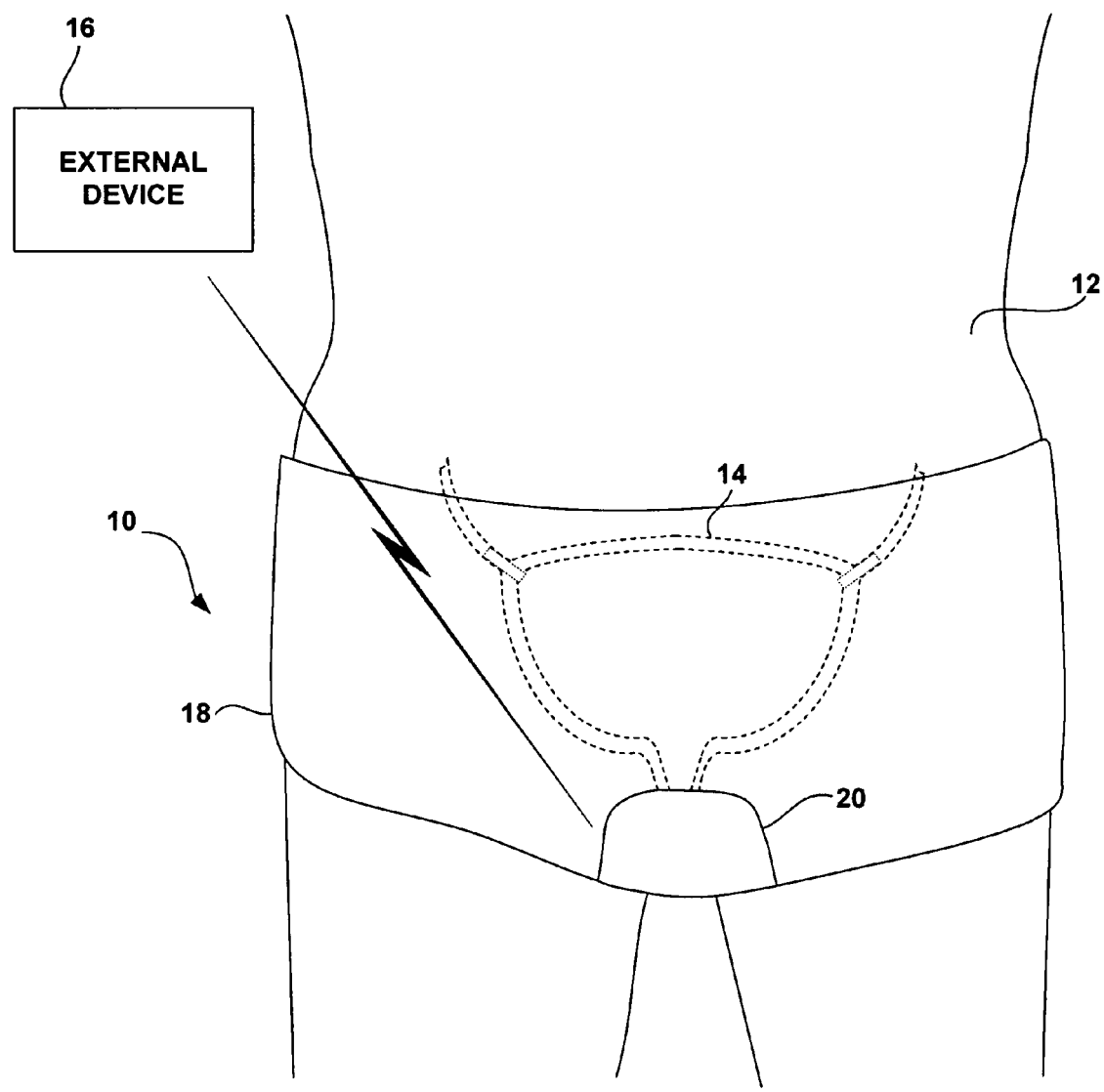
FIG. 1 is a schematic diagram illustrating an external sensing system, incorporating an absorbent pad to detect voiding information.

Urinary incontinence is a condition that affects the quality of life and health of many people. Tracking urinary voiding events may be important in quantifying the number of voluntary or involuntary events a patient has every day as well as qualifying the severity of the urinary incontinence condition. Further, a clinician may collect and monitor samples from the patient to assist in diagnosing the precise condition of the patient. In accordance with this disclosure, an absorbent pad worn by a patient includes one or more sensors that measure one or more parameters associated with urinary voiding events. One or more sensors integrally formed with or carried by the pad measure voiding parameters and store the measured parameters as voiding information in a memory, e.g., locally, or in a separate device. The pad may eliminate the need for a patient to manually track voiding events, such as urine leakage or complete voluntary or involuntary voids and provide urine samples for analysis.

Manually tracking voiding events, e.g., keeping a written or electronic voiding diary, is often undesirable for the patient and providing urine samples can be inconvenient. Keeping the voiding diary takes time out of the patient's day and may be noticed by other people, causing embarrassment to the patient. In addition, manually tracking voiding events may result in voiding information errors. For example, the patient may inadvertently forget to record an event, fail to objectively describe the event, or even purposefully keep false voiding information in the diary. These problems with a voiding diary may undermine the ability of the clinician to properly assess patient condition and prescribe an effective therapy.

As described herein, the patient may wear an absorbent pad that measures urinary voiding parameters as an undergarment or in combination with an undergarment. One or more sensors integrally formed with or carried by the pad measure parameters throughout the day. Each sensor may record and transmit measured parameters to a master module also integrally formed with the pad. Alternatively, the sensors may transmit the measured parameters to an external device. The master module or external device stores the measured parameters as voiding information and may perform processing operations on the information. For example, the master module or external device may detect a physiologic event, e.g., a voiding event, determine the volume, contents, temperature, pH of urine voided by the patient, physical activity such as a cough, or other parameters that may be useful in diagnosing the type of disorder, e.g., stress incontinence or urinary incontinence, based on the information received from the sensors.

The sensors may include various types of sensors such as impedance sensors, strain gauges, temperature sensors, accelerometers, pH sensors, and chemical sensors that measure parameters such as wetness, volume, temperature, pH, and contents of urine voided by a patient as well as the posture and activity of the patient. The sensors may be positioned in a particular area of the pad, referred to as the sensor area. The pad may be constructed to keep the patient pad dry by directing voided urine away from the patient, e.g., by allowing fluid to pass only through the depth of the pad. Accordingly, the sensor area may be strategically positioned in an area of the pad that is most likely to get wet. Within the sensor area, the sensors may be arranged in a two-dimensional sensor layer or a three-dimensional array. In some embodiments, the sensors may form an addressable sensor array that detects wetness by measuring a decrease in resistance between electrodes.

The pad may be constructed to support measurement of the parameters. For example, the pad may be constructed with a transport layer adjacent to the patient that transports fluid voided by the patient to the sensor area, a middle layer that includes the sensors and absorbent material, and a barrier layer that acts as a barrier to prevent fluid voided by the patient from leaking out of the pad. The transport layer is closest to the patient's skin. The barrier layer may reside closest to the patient's clothing. Within the second layer, the sensors may be interwoven with the absorbent material or one or more sensor layers may be separated by one or more absorbent layers. When the sensors are interwoven with the absorbent material, the pad may include more than one layer of absorbent material with interwoven sensors.

In some embodiments, a system according to an embodiment of the invention includes an external device that communicates with the processor, e.g., via a wired or wireless connection, and stores the voiding information as a log that can be viewed by a user. The voiding information may be used to adjust electrical stimulation therapy for incontinence. In this case, the user may manually adjust the stimulation parameters based on the voiding information. In other embodiments, the processor may communicate with an electrical stimulator and automatically adjust electrical stimulation parameters based on the voiding information.

In addition, the pad may be used in conjunction with electrical stimulation therapy for incontinence. For example, the voiding information may be used to adjust stimulation parameters to increase the efficacy of the stimulation therapy. The master module or external device, e.g., a programmer, may automatically adjust stimulation parameters based on the information received from the sensors. Alternatively, a user may view the voiding information via the external device to manually adjust the stimulation parameters. For example, if leakage frequency increases, the patient, clinician, or programmer may increase the intensity of electrical stimulation to prevent or reduce involuntary voiding.

FIG. 1 is a schematic diagram illustrating an external sensing system 10, incorporating a sensor in an absorbent pad to detect voiding information. As shown in FIG. 1, system 10 includes absorbent pad 20, external device 16, and undergarment 18. Undergarment 18 includes absorbent pad 20 in which sensors (not shown) are integrally formed, e.g., interwoven with the absorbent material of the pad or positioned to form one or more sensor layers between layers of absorbent material, to measure urinary voiding parameters. The sensors may record and transmit measured parameters to a master module (not shown), also integrally formed with the pad. Alternatively, the sensors may transmit the measured parameters to external device 16. The master module or external device 16 stores the measured parameters as voiding information and may perform processing operations. For example, the master module or external device 16 may process the information to detect a physiological event, e.g., a voiding event, or determine the volume, contents, temperature, and pH of urine voided by patient 12 as well as the posture and activity of patient 12 during the event, based on the information.

Patient 12 may wear absorbent pad 20 as an undergarment or in combination with undergarment 18 between regular articles of clothing and the skin of the patient so that sensors integrally formed with pad 20 may measure urinary voiding parameters. Voiding parameters includes wetness, time and number of events, posture of patient activity, volume of leaked fluid, contents, temperature, and pH of urine, and other parameters associated urine exiting bladder 14. The contents in urine that may be detected include one or more of hormones, acidity, bacteria, bilirubin, color, cloudiness, glucose, metabolic acid, nitrates, proteins, and puss. The sensors may be positioned within pad 20, e.g., near the opening of the urethra (not shown) of patient 12 to measure urinary voiding parameters. Absorbent pad 20 may allow the urine to spread throughout the pad, which distributes the fluid in the pad and attempts to reduce the amount of wetness against the skin of patient 12. Accordingly, the sensors may be strategically positioned within a particular area of pad 20 that is most likely to absorb urine voided by patient 12. This area is referred to as the sensor area.

Within the sensor area, the sensors may be arranged in a two-dimensional sensor layer or a three-dimensional array of sensors, i.e., two or more sensor layers stacked on top of each other. A sensor layer may be interwoven with absorbent material of pad 20 or one or more sensor layers may be positioned between layers of absorbent material. A sensor layer may comprise any number and type of sensors such as impedance sensors, wetness sensors, pressure sensors, strain gauges, temperature sensors, accelerometers, pH sensors, deformation sensors, or any other sensor that transform mechanical, chemical, or electrical conditions into electrical signals representative of voiding information. Where pad 20 includes a single sensor layer, the sensor layer typically includes various types of sensors for measuring different parameters but may include a single sensor.

Figure 2:
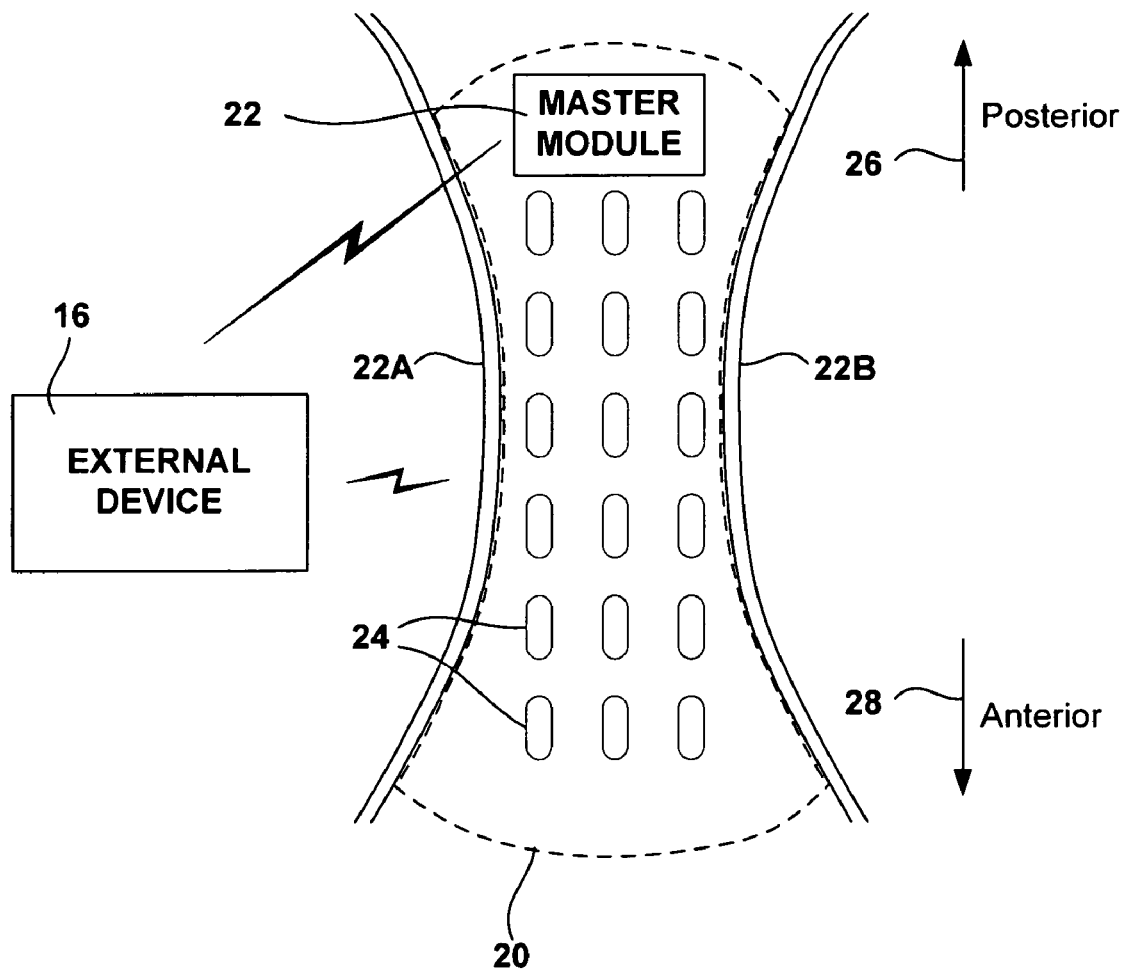
FIG. 2 is a schematic diagram illustrating an absorbent pad of an undergarment with a sensor layer integrally formed within the pad.

FIG. 2 illustrates an absorbent pad with a sensor layer integrally formed within the pad. Where pad 20 includes a three-dimensional array of sensors, i.e., a plurality of sensor layers stacked on top of each other, each sensor layer of the array may include various types of sensors or a single type of sensor. If each sensor layer of the array includes a single type of sensor, it may be advantageous to stack multiple sensor layers on top of each other instead of separating each sensor layer by a layer of absorbent material to increase the chances that each layer is exposed to a sufficient amount of urine absorbed by pad 20 to generate reliable measurements. In other words, it may be advantageous to avoid a scenario in which only the top layer, i.e., the layer closest to the skin of patient 12, is exposed to fluid absorbed by pad 20. By including various types of sensors in each layer, this problem may be substantially reduced or eliminated because each type of sensor in a layer may be exposed to fluid absorbed by pad 20.

Figure 3:
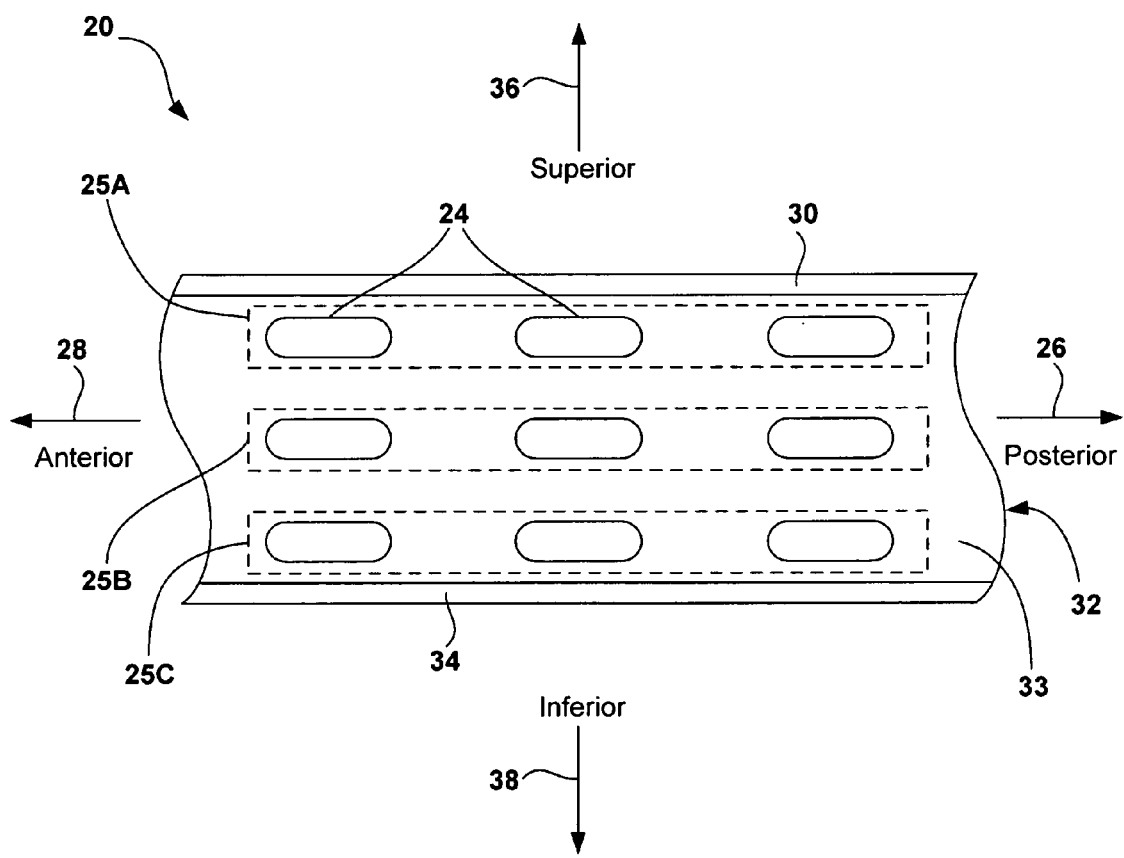
FIG. 3 is a cross-section of an absorbent pad that includes multiple sensor layers.
Figure 7:
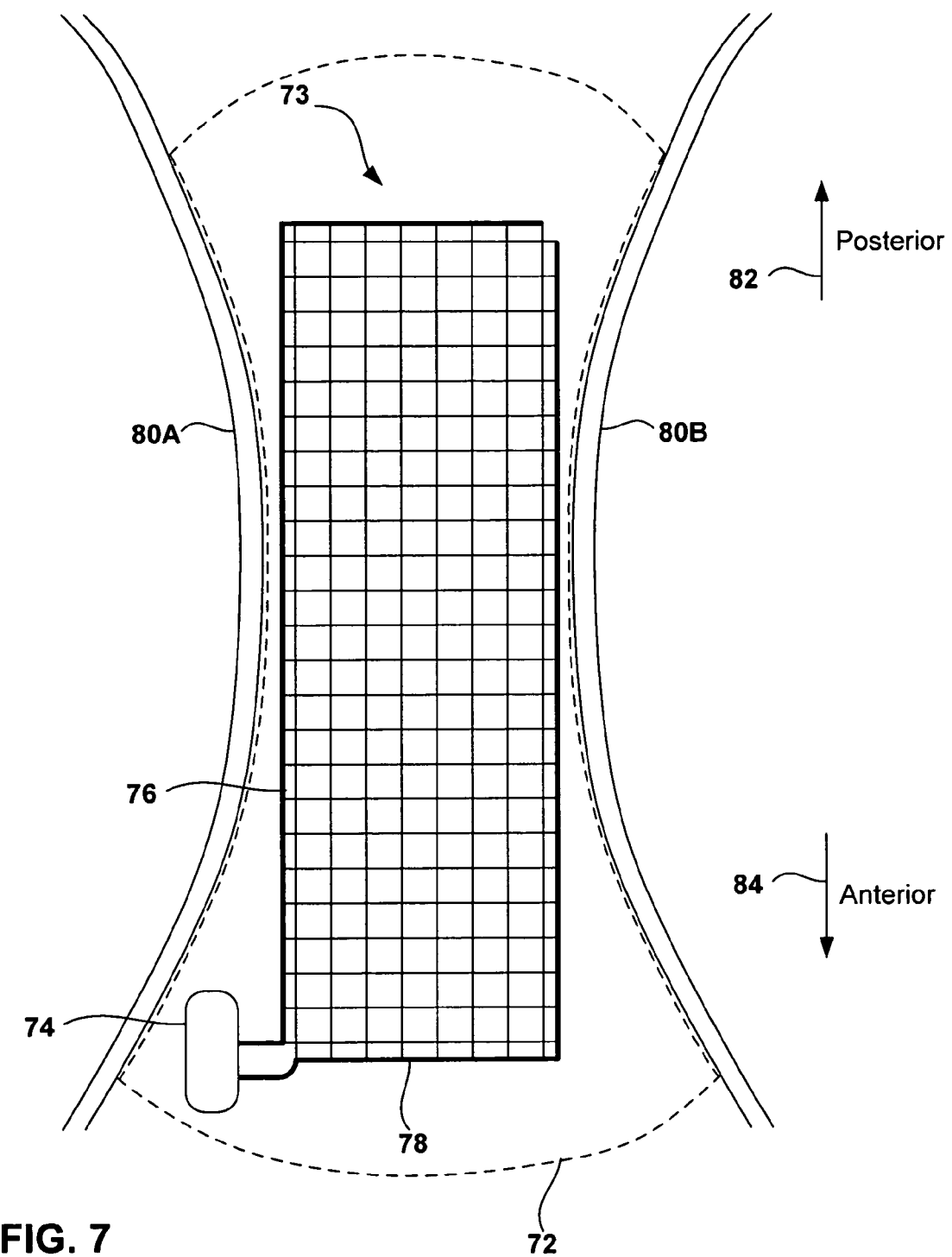
FIG. 7 is a schematic diagram illustrating an absorbent pad, incorporating an addressable sensor array to detect voiding information.

FIG. 3 illustrates an absorbent pad that includes multiple sensor layers, i.e., an three-dimensional array of sensors, integrally formed with the pad. In some embodiments, the sensors may form an addressable sensor array that detects wetness. For example, the addressable sensor array may detect wetness by measuring a decrease in resistance between two electrode groups. In particular, the addressable sensor array may scan the electrode groups, e.g., by column and row address, to detect wetness between the electrodes of the two groups. The two electrode groups may be positioned such that the resistance measured between the electrode groups may be processed to determine a volume of fluid absorbed by pad 20. FIG. 7 illustrates an absorbent pad incorporating an addressable sensor array for detecting wetness.

Absorbent pad 20 may be constructed to support measurement of urinary voiding parameters. For example, pad 20 may be constructed with a transport layer that abuts or is proximate to the skin of patient 12 that transports fluid throughout the pad to reduce the amount of wetness against the skin of patient 12, a middle layer that includes the sensors and absorbent material, and a barrier layer that prevents fluid from leaking out of pad 20. Within the middle layer, the sensors, e.g., one or more sensor layers, may be interwoven with the absorbent material or may be separated by one or more layers of absorbent material. The absorbent material of pad 20 may comprise cotton, cellulose, a hydro-gel, or a hydrophilic material that retains urine. Pad 20 may be capable of retaining an ounce of fluid or greater than 20 ounces of fluid, depending on the material used to construct the absorbent pad. FIGS. 2, 3, 11, and 12 illustrate the construction of an absorbent pad with one or more sensor layers.

Generally, each of the sensors transmits measured parameters to a master module (not shown), also integrally formed with pad 20, or external device 16. In some cases, the sensors may store the measured parameters in local memory and transmit the measured parameters when the sensor can no longer store more information. When the sensors store the parameters in local memory, the sensors may transmit the stored parameters at any time the information is requested by the master module or external device 16, e.g., on a polled basis. Patient 12 or the clinician may interact with external device 16 to cause external device 16 to request the stored parameters from the sensors.

The sensors may transmit the stored parameters to the master module or external device 16 via a wired or wireless connection. For example, the sensors may transmit the stored parameters to external device 16 via a physical connection such as universal serial bus (USB), a serial or data port, or other physical connection or via a wireless interface such as wireless telemetry, Bluetooth, IEEE 802.11(a), (b), (g), or other standard or proprietary wireless interfaces. Alternatively, pad 20 may store voiding information on removable media, such as a flash memory card, that may be received and read by external device 16.

The sensors may also transmit stored parameters to the master module via one of the previously mentioned wireless techniques or may be electrically coupled to the master module and transmit measured parameters to the master module in real-time. When the sensors transmit the stored parameters to the master module, the master module may transmit the information to external device 16 via one of the previously mentioned wireless techniques, physical connection, or via removable media that may be received and read by external device 16.

The master may include a processor which performs processing operations associated with the sensors and memory for storing the measured parameters as information. Processing operations may include detecting a physiologic event, e.g., a voiding event, determining one of the volume, contents, temperature, and pH of urine voided by patient 12, physical activity such as a cough, or other parameters that may be useful in diagnosing the type of disorder, e.g., stress incontinence or urinary incontinence based on the measured parameters received from the sensors. For example, during normal operation, the sensors may detect voiding information that is not an actual voiding event, otherwise known as a false positive. False positives may be produced by activities or situations in which patient 12 participates during normal living. Exemplary false positives may include sweating during an aerobic activity, spilling a glass of liquid on the lap of patient 12, or any other time when urine is not the source of the wetness absorbed by pad 20. The master module may also use the parameters received from the sensors to diagnose a disorder of the patient, i.e., determine if patient 12 suffers from stress incontinence, urinary incontinence, or nocturnal enuresis. As an example, the master module may identify nocturnal enuresis by examining the time at which voiding events occur.

The master module may process the input received from the sensors to determine if the wetness detected by pad 20 is from a voiding event or from a drink spilled on the patient's leg. For example, the master module may compare one or more characteristics of the fluid to urine characteristics to identify the fluid as urine in order to reduce any false positive detection. The master module may also determine if wetness absorbed by pad 20 is a result of sweating during an aerobic activity by examining input received from an accelerometer. If the master module determines that a voiding event occurred, it may associate a time stamp with the voiding event and store the event in memory. The processor may also determine the volume of fluid absorbed by pad 20, e.g., by processing wetness information from one or more sensors, strain gauges, or an addressable sensor array. The master module may store the information within memory as a voiding log. As mentioned previously, the master module may transmit the voiding log or information received from the sensors to external device 16 via a physical or wired connection or removable media.

Similar to the master module, external device 16 may also include a processor that performs processing operations associated with the sensors and memory for storing information received from the sensors or the master module. Hence, processing of sensor information may be performed within the sensor pad, within the external device, or both. External device 16 may function, i.e., perform processing operations, as discussed with respect to the master module. However, external device 16 may include a user interface that enables patient 12 or a clinician to view each component of the voiding information contained in the voiding log. A component may be one voiding event. External device 16 may allow patient 12 or the clinician to modify a component of the voiding log to correct any incorrect voiding information.

Accordingly, pad 20 may be used primarily as a diagnostic tool to provide objective patient 12 condition information for the clinician. The clinician may use the voiding log to determine an appropriate course of treatment, which may or may not include stimulation therapy. In addition to its role in storing and presenting a voiding diary or log, external device 16 may also function as a programmer in embodiments in which pad 20 is used as a feedback system for delivering stimulation therapy to patient 12 for urinary incontinence.

Figure 17:
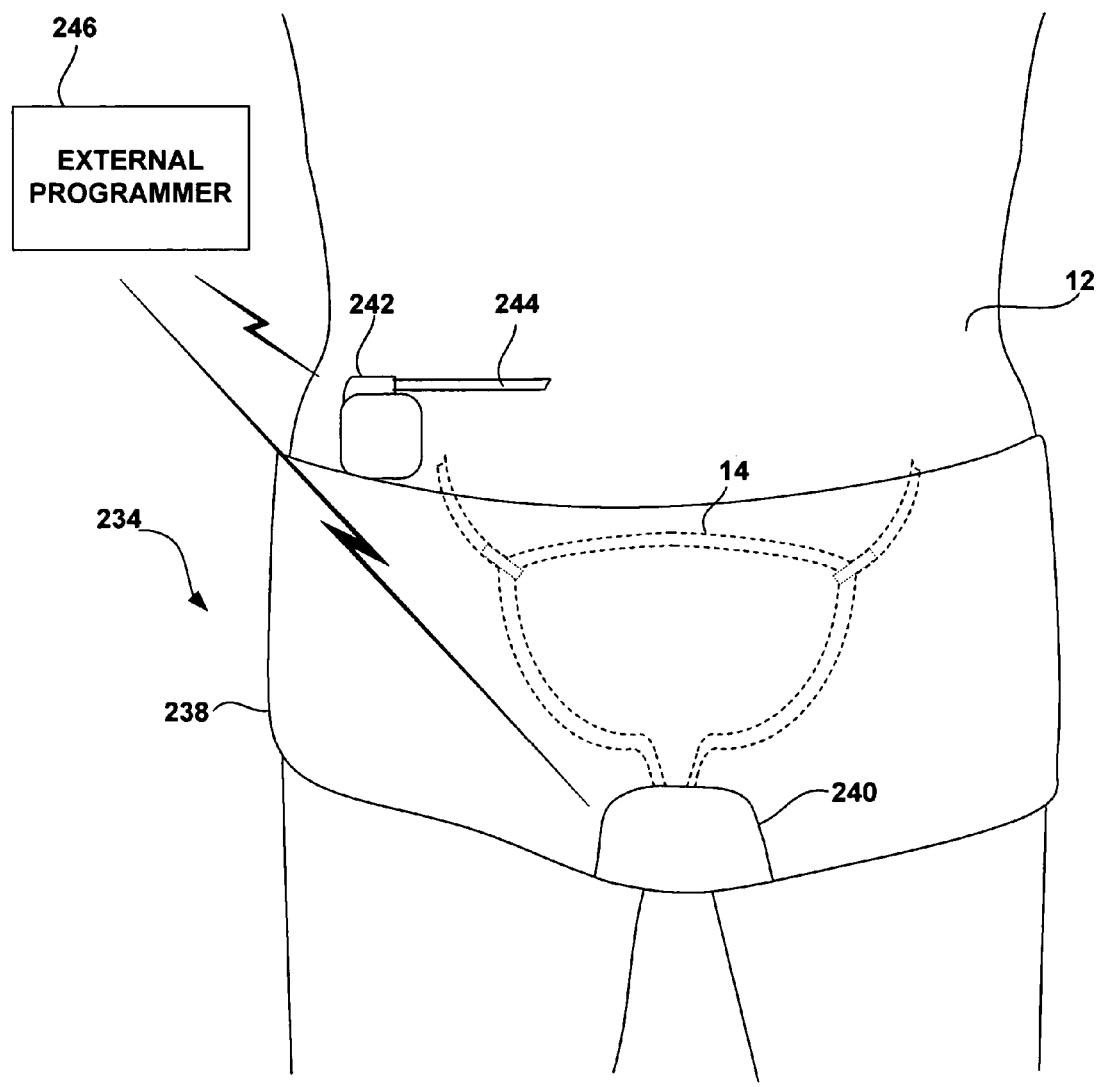
FIG. 17 is a schematic diagram illustrating a stimulation feedback system, incorporating an implanted stimulator that delivers stimulation therapy based upon voiding information from an absorbent pad.

FIG. 17 illustrates a stimulation feedback system incorporating an implanted stimulator that delivers stimulation therapy based upon voiding information from an absorbent pad. In such embodiments, the clinician or patient 12 may use external device 16 to review the voiding information and adjust one or more stimulation parameters that define the stimulation therapy accordingly. Example stimulation parameters include an electrode configuration, a pulse rate, a pulse width, and voltage amplitude or current amplitude. Electrode configuration may refer to both a combination of selected electrodes and polarities of the electrodes, i.e., as cathode or anode.

The clinician may interact with external device 16 to manually adjust the stimulation therapy to reduce the frequency or number of voiding events identified in the voiding log. Alternatively, external device 16 may automatically adjust stimulation parameters based on the voiding information. External device 16 may include instructions that identify which parameters to adjust when a certain type of voiding information is detected. Alternatively, external device 16 may provide suggested adjustments to the clinician or patient 12, and the adjustments may not take effect until the clinician or the patient agrees with the suggestion. When pad 20 includes a master module, the master module may also automatically adjust stimulation parameters based on the voiding information.

Because undergarment 18 and, more specifically, absorbent pad 20 may come into contact with urine or other bodily fluids, the undergarment may be either disposable or washable. If undergarment 18 is disposable, patient 12 may discard the undergarment and everything attached as refuse. Patient 12 may use a new undergarment 18 if a voiding log is still to be stored. If undergarment 18 is washable, patient 12 may reuse the undergarment after the undergarment is cleaned to remove any urine or other bodily fluids. In either case, pad 20 may stay with undergarment 18, but patient 12 may need to remember to transmit the voiding log from pad 20 to external device 16 prior to disposal to prevent risk of loss of detected voiding information.

In alternative embodiments of system 10, pad 20 may not be included in undergarment 18. Pad 20 may be gender specific, with the sensor area located near the middle for female anatomy and near the anterior side for male anatomy. In addition, pad 20 may comprise a condom-like device that males may use to cover the penis. In this case, the sensor area may be located at the distal tip of the device. Other embodiments may also include a pad 20 taped to the skin of patient 12 or undergarment 18, trapped between clothing and the skin, attached to the inside of other clothing, sutured to the skin of the patient, or held to the skin of the patient via a strap.

FIG. 2 is a schematic diagram illustrating absorbent pad 20 with a sensor layer integrally formed within pad 20. In the illustrated example, pad 20 is shown as it may be positioned between undergarment 18 and skin of patient 12. Undergarment 18 includes elastic bands 22A and 22B (collectively 'elastic bands 22') which help to retain any voided urine from leaking out from the sides of undergarment 18. Pad 20 is shaped to catch and retain any urine that is voided from patient 12. Generally, the shape of absorbent pad 20 allows at least a portion of the absorbent pad to be placed adjacent to the opening of the urethra in either a male or female patient 12. Absorbent pad 20 allows the urine to spread throughout the pad, which distributes the fluid in the pad and attempts to reduce the amount of wetness against the skin of patient 12. As mentioned above, absorbent pad 24 may be constructed of cotton, cellulose, a hydro-gel, or some other hydrophilic material that retains urine.

The sensor layer comprises a plurality of sensors 24 arranged in a two-dimensional layer that transmit measured parameters to a master module 22. As shown in FIG. 2, sensors 24 may be evenly positioned relative to each other over the entire surface of pad 20. Because pad 20 may allow urine to spread through the pad to reduce the amount of wetness against the skin of patient 12, each of sensors 24 may be exposed to a sufficient amount of fluid absorbed by pad 20. As mentioned above, absorbent pad 24 may be constructed of cotton, cellulose, a hydro-gel, some other hydrophilic material that retains urine. However, the invention is not so limited. Rather, instead of being distributed over the entire surface or a large portion of the surface of pad 20, sensors 24 may be located over a substantially smaller portion of pad 20 referred to as the sensor area. For example, sensors 20 may be positioned or clustered to form a layer located near the urethra of the patient. In this manner, the probability of all of sensors 20 being exposed to urine voided by the patient may be increased. In gender specific applications, the sensor area may be moved in the anterior direction for males according to arrow 29 and the sensor area may be moved in the posterior direction according to arrow 27 for females.

Sensors 24 may comprise any number and type of sensors such as impedance sensors, wetness sensors, pressure sensors, strain gauges, temperature sensors, accelerometers, pH sensors, deformation sensors, or any other sensor that transforms mechanical, chemical, or electrical conditions into electrical signals representative of voiding information. A sensor layer may include various types of sensors for measuring different voiding parameter. For example, a sensor layer may include an appropriate sensor for each parameter to be measured. In other words, if the parameters to be measured are wetness, temperature, volume, and contents of leaked fluid as well as the posture and activity of the patient, a sensor layer may include an impedance sensor, a temperature sensor, a strain gauge, and an accelerometer, respectively. In some embodiments, a sensor layer may comprise a plurality of groups of electrodes in which each group of electrodes includes a plurality of electrodes that measure the same parameter. Each group of electrodes, however, may measure a different parameter. In this manner, several measurements may be obtained for the same parameter, thereby increasing the reliability of the measurement.

While each of sensors 24 are generally oval shaped in the example of FIG. 2, each of sensors 24 may be constructed in a number of different shapes. Sensors 24 may be constructed as a flexible flat rectangle, a rigid curved shell, a sphere, a rounded and flat triangle, or any other shape capable of housing the components of sensors 24.

A sensor layer may include a single type of sensor when pad 20 includes a plurality of sensor layers. In this case, each sensor layer may measure a different parameter. The sensor layers may be stacked directly on top of each other of with an absorbent layer between each sensor layer to form a three-dimensional array. A three-dimensional array of sensors may also comprise two layers of wires that form a grid of virtual electrodes. For example, the grid of virtual electrodes may form an addressable sensory array used to determine a volume of fluid absorbed by pad 20 by measuring a decrease in resistance for each of the virtual electrodes. FIG. 7 illustrates an exemplary addressable sensory array. In any case, a sensor layer may be integrally formed with an absorbent material of pad 20 or may be positioned between layers of absorbent material.

Each of sensors 24 may transmit measured parameters to master module 22, also integrally formed with pad 20, or external device 16. For example, each of sensors 24 may be electrically coupled to master module 22 via corresponding electrical conductors (not shown). In this case, the electrical signal produced by the sensor may be monitored in real-time by master module 22. Moreover, master module 22 may selectively drive individual sensors 24 to obtain information. For example, master module 22 may sequentially scan sensors 24.

Master module 22 includes a memory for storing the input received from sensors 24 as voiding information. In another example, each of sensors 24 may include a telemetry circuit and transmit information to master module 22 or external device 16 wirelessly. Alternatively, sensors 24 may simply be wired directly to master module 22. Sensors 24 may store the information in a local memory and transmit the information to master module 22 or external device 16 when the information can no longer be stored in respective sensors 24 or at any time the information is requested by master controller 26 or external device 16. In other embodiments, each sensor 34 may be addressable through a wire connecting each sensor in series. Sensors 24 may alternatively be connected in parallel or in groups, as each sensor 24 may hang off of the wire connecting the sensors. Master module 22 may address each sensor and receive a measured parameter from the addressed sensor. In this network of sensors 24, data may be directly transmitted to master module 22 with substantially no storage within sensors 24.

Patient 12 or the clinician may interact with external device 16 to cause external device to request information from sensors 24. Master module 22 may be pre-programmed to request information from sensors 24 at regular time intervals. In some embodiments, pad 20 may not include master module 20. In this case, sensors 24 transmit information to external device via one of the previously discussed wireless or wired connections.

Again, when sensors 24 transmit information to master module 22, master module 22 may transmit the information to external device 16 via a physical or wireless connection. Master module 22 may transmit information to external device 16 when the information can no longer be stored on master module 22 or at any time when external device 16 requests the information.

As previously discussed, master module 22 may include a processor that performs processing operations associated with sensors 24 and memory for storing the input received from sensors 24. Again, master module 22 may store the information received form sensors 24 as a voiding log and transmit the voiding log to external device 16 as previously described. Alternatively, master module 22 may transmit sensor information to an external device, which then generates or updates a voiding log.

Processing operations within master module 22 or an external device may include detecting a voiding vent, determining if the wetness absorbed by pad 20 is from a voiding event or from a drink spilled on the patient's leg, determining the contents of urine absorbed by pad 20, and determining a volume of fluid absorbed by pad 20. In some embodiments, pad 20 may be incorporated in a feedback system for delivering stimulation therapy to patient 12 for urinary incontinence. In such embodiments, master module 20 may automatically adjust parameters that define the stimulation therapy to increase the efficacy of the therapy. In this case, master module 22 may store instructions that identify which parameters when a certain type of voiding information is detected.

External device 16 may include a processor and memory and function in a similar fashion as master module 22. In particular, external device 16 may perform similar processing operations, such as detecting voiding events, determining characteristics of urine voided by the patient, and automatically adjusting stimulation parameter, and store information received from sensors 24 or master module 22 as a voiding log. However, external device 16 may further include a user interface that enables patient 12 or a clinician to view each component of the voiding information contained in the voiding log and allow patient 12. Additionally, the clinician may interact with external device 16 to manually adjust the stimulation therapy based on the voiding information. External device 16 may also include instructions that identify which parameters to adjust when a certain type of voiding information is detected or provide suggested adjustments that take effect only after the clinician or patient agrees with the suggestion, e.g., by selecting a "yes" or "no" box from a display.

FIG. 3 is a cross-section of absorbent pad 20 including multiple sensor layers 25A-25C (collectively referred to herein as "sensor layers 25"). Each of sensor layers 25 includes a plurality of sensors 24 as previously described with respect to FIG. 2. Sensor layers 25 form a three-dimensional array of sensors that measure urinary voiding parameters and transmit the parameters to a master module or external device (not shown to avoid confusion), such as master module 22 (FIG. 2) and external device (FIGS. 1 and 2).

The cross section-section of pad 20, as shown in FIG. 3, illustrates three distinct layers, i.e., a transport layer 30, an absorbent middle layer 32, and a bottom layer 34 that prevents fluid absorbed by middle layer 32 from leaking out of pad 20. Transport layer 30 abuts or is proximate to the skin of patient 12 and distributes urine over layer 30 to allow urine to spread throughout absorbent middle layer 32 thereby reducing the amount of wetness against the skin of patient 12. In other words, instead of allowing urine leaked by patient 12 to be absorbed directly by middle layer 32 which may result in a high concentration of urine absorbed near the urethra of the patient and a substantially lower concentration absorbed at the outer boundaries of pad 20, transport layer 30 causes urine leaked by patient 12 to be distributed evenly over layer 30 and thereby absorbed throughout pad 20. As a result, transport layer 30 causes urine to be absorbed substantially evenly throughout absorbent middle layer 32.

Figure 11:
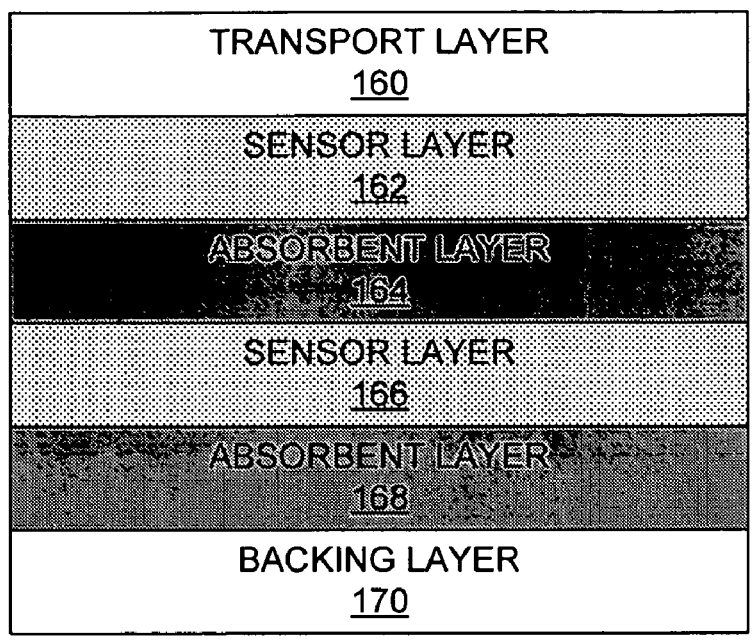
FIGS. 11 and 12 are schematic diagrams illustrating embodiments of the layered construction of the absorbent pad of FIG. 10.
Figure 12:
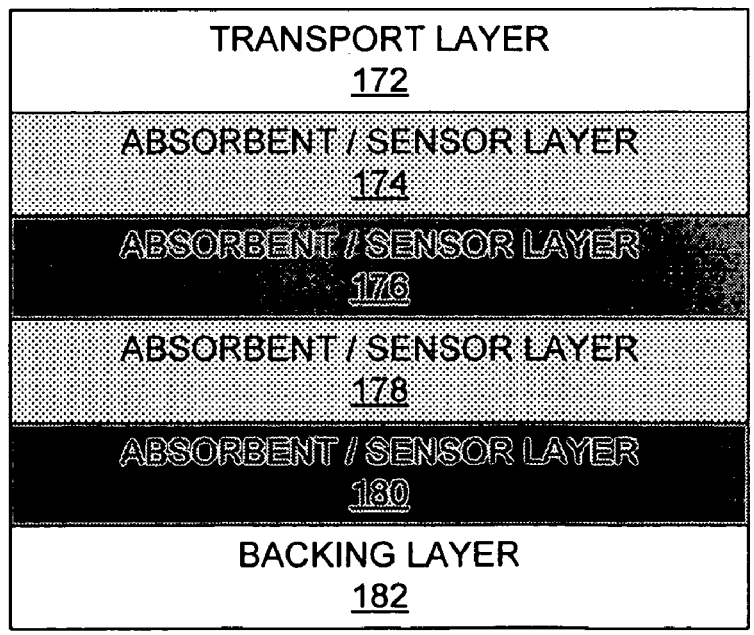

Middle layer 32 includes an absorbent material 33 and one or more sensor layers 25. As shown in FIG. 3, sensor layers 25 may be interwoven with absorbent material 33. Alternatively, sensor layers 25 may be positioned between layers of absorbent material 33. FIGS. 11 and 12 illustrate layered construction of a middle layer of an absorbent pad. Absorbent material 33 may comprise cotton, cellulose, a hydro-gel, or a hydrophilic material that retains urine. Absorbent material 33 may enable pad 20 to retain an ounce of fluid or greater than 20 ounces of fluid, depending on the material used to construct the pad and the size of the pad.

Absorbent material 33 may allow urine or any fluid to only be absorbed in an inferior direction, i.e., away from the patient, indicated by arrow 38. In other words, once a fluid has been absorbed to a particular depth, the fluid is prevented from being re-absorbed in a superior direction, i.e., towards the patient, indicated by arrow 36. Directional absorption may be achieved by an oriented wicking structure that is formed by fibers or other materials within absorbent material 33.

As previously described with respect to FIG. 2, each one of sensor layers 25 may include any number and type of sensors. In particular, each one of sensor layers 25 may include various types of sensors or a single type of sensor. Because a voiding event may not produce an amount of urine that results in middle layer 32 absorbing the urine through its thickness, it may be advantageous to form each of sensor layers 25 with various types of sensors. By including different types of sensors within each of sensor layers 25, the probability of each of the sensors of the top (superior) layer may be increased because the amount of urine voided by the patient may only result in a shallow depth of absorption, i.e., the urine may not be absorbed through the depth of middle layer 32. However, each of sensor layers 25 may include a single type of sensor and each of sensor layers may measure a different parameter. In this case, middle layer 32 may be constructed such that even a small amount of urine may be absorbed through the thickness of pad 20.

Although sensor layers 25 are shown in FIG. 3 as being distributed evenly throughout the thickness of pad 20 and, more particularly middle layer 32, sensor layers 25 may be sufficiently reduced in size such that the total thickness of the sensor layers is small with respect to the thickness of the pad. For example, sensors 24 may have a capsule-like shape with a thickness of approximately 1 to 5 mm. Consequently, each sensor layer may be sufficiently exposed to urine even when a small amount is voided by the patient. Sensors 24 may measure parameters, store measured parameters, and transmit measured parameters to a master module or external device as previously discussed with respect to FIG. 2.

Figure 4:
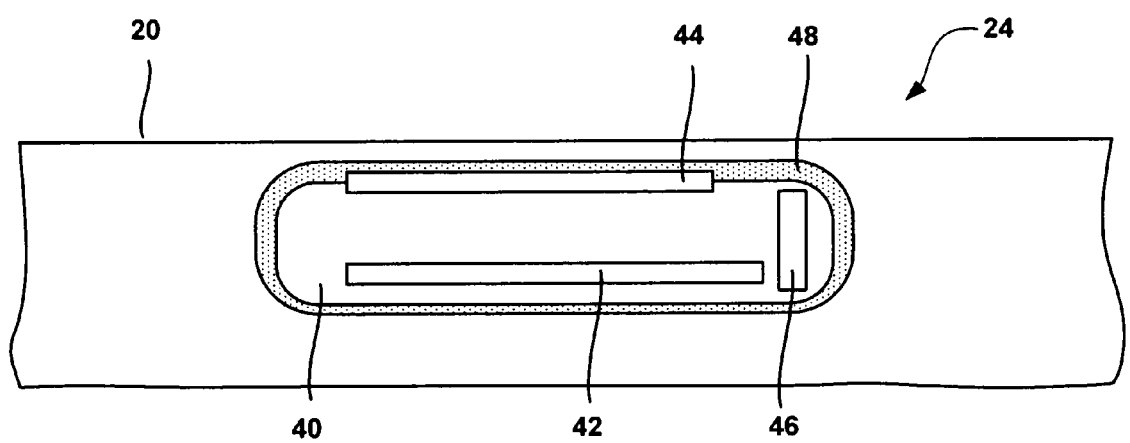
FIG. 4 is a cross-section of a sensor that is integrally formed within an absorbent pad.

FIG. 4 is a cross-section of an example sensor that is integrally formed within an absorbent pad. As shown in FIG. 4, sensor 24 is secured by absorbent pad 20. As described above, multiple sensors 24 may be provided in absorbent pad 20. Sensor housing 40 of sensor 24 is embedded in absorbent pad 20, e.g., between layers of the pad. In the example of FIG. 4, sensor 24 includes circuit board 42, power source 46, and sensing element 44. Sensor housing 40 may be in the shape of a rounded capsule, as shown in FIG. 4, and includes a smooth surface. Sensing element 44 extends from housing 40. Sensing element 26 may detect a change in impedance, e.g., between two or more electrodes of the sensing element. In this manner, sensing element 44 detects voiding information from a fluid, e.g. urine, present in absorbent pad 20. In other embodiments, sensing element 44 may include a strain gauge to detect pressure, which slightly protrudes from the housing to sense deformation changes in absorbent pad 20.

Sensor 24 rests in a cavity 48 formed within absorbent pad 20. Cavity 48 may be formed between upper and lower layers of absorbent pad 20 or formed as a hollowed out region of a bed of fibers within the absorbent pad. In some embodiments, sensor 24 may have a capsule-like shape, and may have a length of approximately 2 to 10 mm, a width of approximately 2 to 5 mm, and a thickness of approximately 1 to 5 mm. The capsule-like shape may produce a circular or oval-like cross-section, in which case sensor 24 may have a diameter or major diameter of approximately 1 to 5 mm, rather than width and height dimensions. However, a capsule-like shape is merely described for purposes of example.

Sensing element 44 senses an impedance change in the space around sensor 24 from fluid within absorbent pad 20 as urine is voided from bladder 14. Sensing element 44 may detect electrical differentials, or other detectable parameters of the fluid. In some embodiments, fluid characteristics such as pH or electrolyte concentration may also be detected using pH or other chemical sensors. Processing electronics on circuit board 42 detect changes sensed by sensing element 44. Circuit board 42 communicates the voiding information to external device 16 or another sensor 24, e.g., a master module, by wireless telemetry. Circuit board 42 also controls the operation of sensor 24.

Embedding sensor 24 within absorbent pad 20 may be a simple method for securing the sensor 24. As bladder 14 voids urine, sensing element 44 detects a fluid within absorbent pad 20 and indicates that voiding has occurred. For example, a decrease in impedance of absorbent pad 20 may indicate that a fluid is present to more easily conduct the electrical current between two electrodes of sensing element 44. Although sensing element 44 may include electrodes, many other types of sensing components may be used to sense voiding, such as a strain gauge that measures deformation of absorbent pad 20, which indicates that the pad is swelling with urine.

Sensor 24 may have a biocompatible housing, which may be formed from titanium, stainless steel or other materials that resist corrosion. In some embodiments, sensor 24 may carry one or more expandable elements that help to anchor the sensor within absorbent pad 20. The expandable elements may be constructed from a hydro-gel material. During implantation, the expandable elements are in a dehydrated state, in which the expandable elements are smaller. But when implanted in the body of a patient, the expandable elements absorb water and assume a hydrated state. In the hydrated state, the expandable elements have a larger perimeter and may embed within the surrounding material of absorbent pad 20. Expansion of the expandable elements resists migration of the sensor 24 within absorbent pad 20. When allowed to dry, sensor 24 may be securely embedded within absorbent pad 20.

Figure 5:
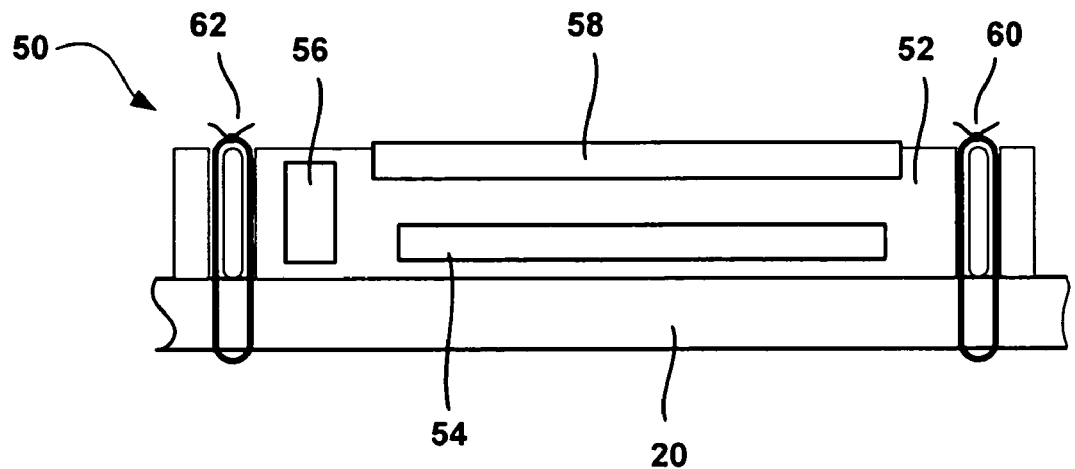
FIG. 5 is an enlarged schematic diagram illustrating a sensor sewn to a layer of an absorbent pad.

FIG. 5 is an enlarged schematic diagram illustrating a sensor sewn to a layer of an absorbent pad. As shown in FIG. 5, sensor 50 represents another exemplary embodiment of a sensor, e.g. sensor 24, deployed within a patient's undergarment to detect voiding events. Sensor 50 is sutured, i.e., sewn, to absorbent pad 20, or in some cases, directly to undergarment 18 or another article of clothing. Sensor housing 52 is attached to absorbent pad 20 and includes circuit board 54, power source 56, and sensing element 58. Sutures 60 and 62 are used to attach bladder sensor 50 to absorbent pad 20. Although only two sets of sutures can be shown in FIG. 5, sensor 50 may include four or more sets, one at each corner of the rectangular shaped sensor.

Circuit board 54, power source 56 and sensing element 58 may all be similar to circuit board 42, power source 46 and sensing element 44 of FIG. 4. In addition, sensor housing 52 may be functionally similar to sensor housing 40 of FIG. 4. Differences between these components of each embodiment may relate to only the size or shape of each component. As in some embodiments of sensing element 44, sensing element 58 may include two or more electrodes that detect a change in impedance of absorbent pad 20 as the absorbent pad swells with fluid. Sensing element 58 sends the voiding information to circuit board 54. Circuit board 54 wirelessly communicates the voiding information to external device 16. Circuit board 54 also may control the operation of sensor 50.

Once sensor 50 is placed on the external surface of absorbent pad 20, the operator uses three to tie sensor 50 to absorbent pad 20, which is illustrated by sutures 60 and 62 in FIG. 5. The sutures may or may not penetrate through absorbent pad 20, and no urine will escape absorbent pad 20 in either case. In some embodiments, metal or plastic staples may be used to fix sensor 50 to absorbent pad 20 instead of nylon thread. In accordance with this disclosure, multiple sensors 50 may be placed around absorbent pad 20 to generate an average expansion or contraction of the entire bladder.

Once attached to absorbent pad 20, sensing element 58 may be securely forced against absorbent pad 20. As absorbent pad 20 expands and contracts, sensing element 58 may sense the changed pressure by absorbent pad 20 and indicate a change in size of the pad. Similar to sensing element 44 of FIG. 4, many other types of sensing components may be used to detect voiding information of patient 12. However, electrodes that detect a change in impedance are described herein for purposes of illustration. Sensing element 58 may also be chemical sensors in other embodiments.

As an example of another fixation mechanism, sensor 50 may be provided with an adhesive backing on a surface of housing 52 for permanent or removable attachment to absorbent pad 20 or undergarment 18. As a further alternative, one or more surfaces of housing 52 may carry one half of a reciprocal hook-and-loop fastening device. Absorbent pad 20 may carry the other half of the hook-and-loop fastening device, which may be sewn or adhesively attached to the pad or undergarment.

In this manner, sensor 50 may be removably attached to pad 20 via the hook-and-look attachment. A hook-and-loop fastener device, such as a Velcro® device, may be used. Other examples of removable attachment devices include snap-fit fasteners, press-fit fasteners or the like. Removable attachment devices may permit sensors 50 to be reused, e.g., by removing and reattaching the sensor to the different undergarments or pads, or to the same undergarment or pads between washing.

Figure 6:
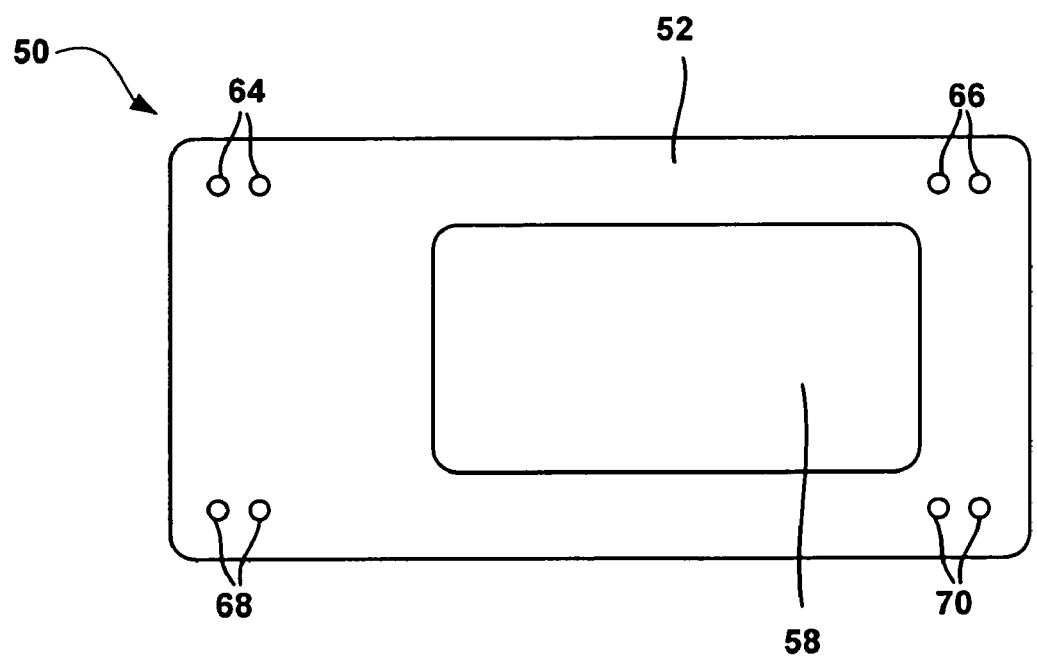
FIG. 6 is an enlarged, bottom view of the sensor of FIG. 5.

FIG. 6 is an enlarged, bottom view of the sensor of FIG. 5. As shown in FIG. 6, sensor 50 includes sensor housing 52 and sensing element 58. Fixation holes 64, 66, 68 and 70 are voids in housing 52 and allow suture to be passed through housing 52 in order for sensor 50 to be attached to absorbent pad 20. Sensing element 58 may occupy a majority of the surface area of bladder sensor 50 that faces patient 12. While sensing element 58 is rectangular in shape, the electrodes may be formed of any symmetric or asymmetrical shape, preferably circular in shape. Sensor 50 may have a length of approximately 2 to 15 mm, a width of approximately 2 to 10 mm, and a thickness of approximately 2 to 10 mm.

Fixation holes 64, 66, 68 and 70 each contain a pair of passages through housing 52. Each pair of passages is located near a corner of housing 52. An operator may pass a suture through these holes to attach housing 52 to absorbent pad 20 in a desired location of absorbent pad 20. While fixation holes 64, 66, 68 and 70 each contain two holes, other embodiments may include more or less holes in housing 52. For example, each corner of housing 52 may only contain one hole. Thread would then pass through the hole and around the outside of housing 52. As a further example, each corner may contain three holes for further securing housing 52 to absorbent pad 20.

Other fixation methods to secure bladder sensor 50 to absorbent pad 20 may include other structures different than thread. For example, each corner of housing 52 may contain a barbed needle or helical screw that ejects from housing 52 into absorbent pad 20. The barbed needles may secure sensor 50 to absorbent pad 20 without lengthy attachment procedures. Also, as mentioned above, adhesives or hook-and-loop fasteners may be used as an alternative, or in addition to, mechanical fasteners such as staples, needles or screws. In alternative embodiments, sensor 50 is attached to the side of absorbent pad 20 facing away from patient 12. In this case, sensing element 58 would contact a surface of absorbent pad 20 to detect the voiding information.

FIG. 7 is a schematic diagram illustrating an absorbent pad, incorporating an addressable sensor array to detect voiding information. As shown in FIG. 7, absorbent pad 72 includes an addressable sensor array 73 that measures resistances, i.e., a voiding parameter, within the absorbent pad to determine the volume of fluid voiding by patient 12. Addressable sensor array 73 includes sensor 74 that houses a processor and other components that operate the array. Sensor array 73 also includes a first electrode group 76 and a second electrode group 78 that are oriented perpendicular to each other. Each electrode group 76 and 78 include an electrode at the intersection of each group, and the resistance is measured between each of these electrodes, or electrode set. Sensor 74 scans each electrode set to detect wetness, and/or determine a fluid volume based on the number of electrodes sets that indicate a resistance indicative of wetness during the scan. In addition, the location of the fluid may also be determined.

In the example of FIG. 7, electrode group 76 and electrode group 78 are separated by a predetermined distance of absorbent material within the absorbent pad 72. When the absorbent material is dry, the resistance is high between each electrode set of the groups 76 and 78. If fluid swells in the absorbent material between each electrode of an electrode set, the measured resistance decreases to indicate that fluid is present. By adding the number of electrode sets measuring decreased resistances and calculating the area of electrode sets indicating that fluid is present, sensor 74 may determine an approximate volume of fluid, or urine, present in absorbent pad 72.

In some embodiments, absorbent pad 72 may include multiple addressable sensor arrays 73 in multiple layers. In this manner, the sensor arrays 73 may create a three dimensional array that more accurately measures the volume of fluid voiding by patient 12. This information may be important for precise characterization of the voiding occurring during the diagnosis or therapy period of patient 12.

Figure 8:
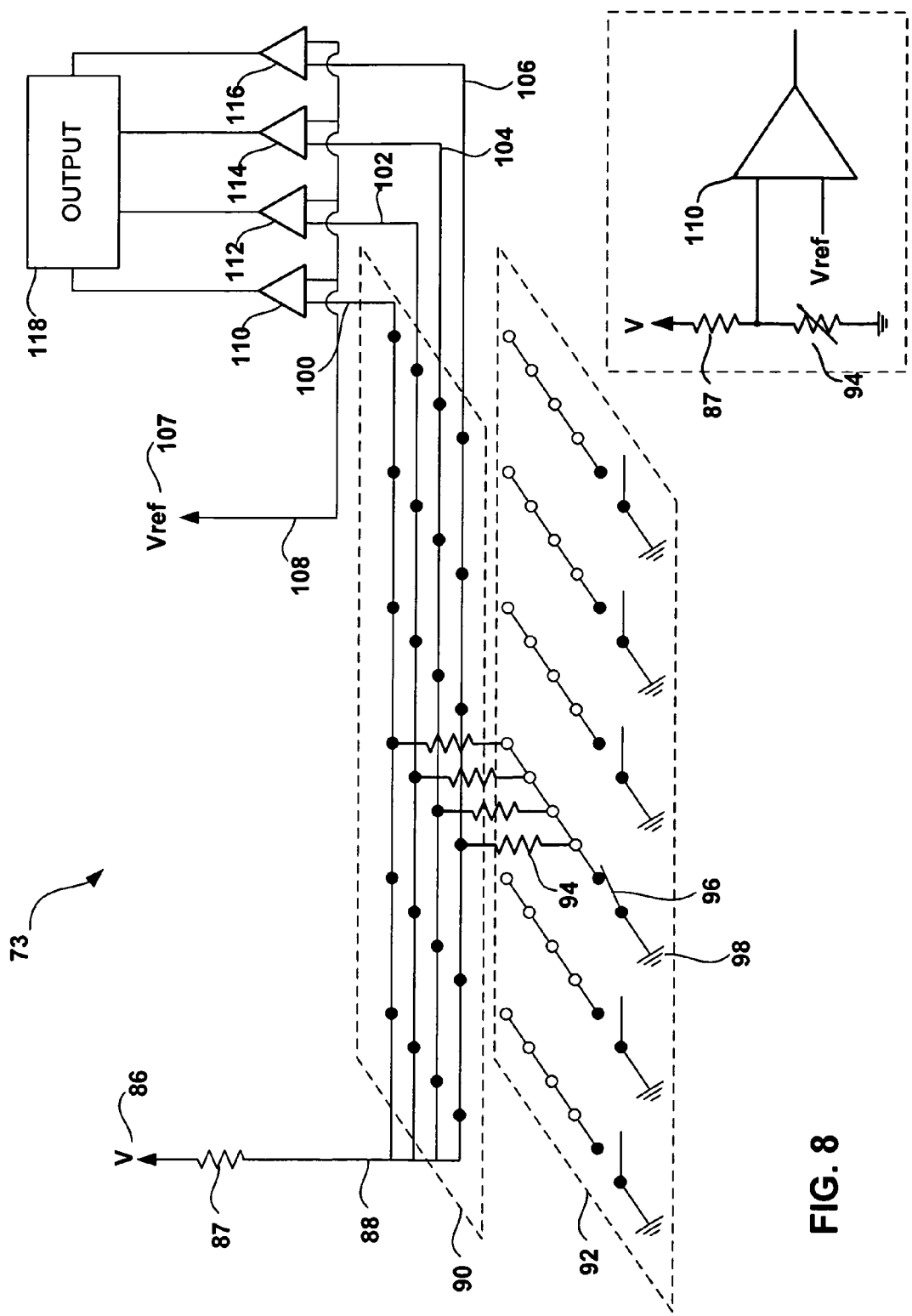
FIG. 8 is a schematic diagram illustrating the components of the addressable sensor array of FIG. 7.

FIG. 8 is a schematic diagram illustrating the components of the addressable sensor array of FIG. 7. As shown in FIG. 8, addressable sensor array 73 includes the electrical components to measure changes in resistance between each electrode set. Voltage source 86 provides voltage to first electrode group 90 through resistor 87 and input 88. Input 88 splits into multiple wires that each include multiple electrodes that transmit the voltage into the absorbent layer. Below first electrode group 90 is second electrode group 92. Hence, multiple wires interconnecting the various electrodes to sensing circuitry may be embedded within the sensor pad. Electrode group 92 includes wires perpendicular to the wires of first electrode group 90. Each wire of second electrode group 92 includes a switch 96 and ground 98. One switch 96 of second electrode group 92 is closed at a time to measure the resistance between electrode sets associated with one wire of the second electrode group.

When switch 96 is closed, resistance 94 of the absorbent material is measured for each electrode set associated with the closed switch 96. The current from voltage source 86 travels between an electrode of first electrode group 90 to the associated electrode of second electrode group 92 and to ground 98 if fluid is present to indicate a decreased resistance of the absorbent material. If the absorbent material is not wet, substantially little or no current flows between the electrode set and a significant voltage drop is not measured.

The voltage at lines 100, 102, 104, and 106 are representative of the changes in voltage due to any voltage drop from switch 96 being closed. Voltage source 107 provides a reference voltage through line 108 that is used at each comparator 110, 112, 114, and 116. Each voltage from lines 100, 102, 104, and 106 is sent to respective comparators 110, 112, 114, and 116 to measure changes in the voltage of each line to the reference voltage from voltage source 107. The voltage from voltage sources 86 and 107 may be the same or different, as long as the initial voltage from each source is known. The difference in voltage for each comparator 110, 112, 114, and 116 is sent to output 118 where the magnitude of the measured difference in voltage, if any, is calculated and used to determine if fluid is located in the absorbent material between any of the electrode sets of first electrode group 90 and second electrode group 92. Hence, the difference signal indicates whether the absorbent material is wet or not. The larger circuit diagram within the dotted box provides a simplified example of the circuit for one electrode set of first electrode group 90 and second electrode group 92. Voltage (V) is sent through resistor 87 and into an absorbent material simplified by variable resistor 94 before the ground connection. The voltage from resistor 87 is compared to the reference voltage (Vref) in comparator 110. The resulting output voltage is used to measure the wetness of the absorbent material between the electrode set.

In some embodiments, switch 96 stays closed until output 118 measures a change in resistance that indicates fluid has been voided by patient 12. Once fluid has been detected, sensor 74 scans all electrode sets of addressable sensor array 73 to measure all resistances of absorbent pad 72. In this manner, sensor 74 may require less power to change each switch 96 when no fluid is present. In operation, switches 96 are sequentially opened and closed to scan the electrode sets in the sensor array for resistance values that indicate wetness.

Figure 9:
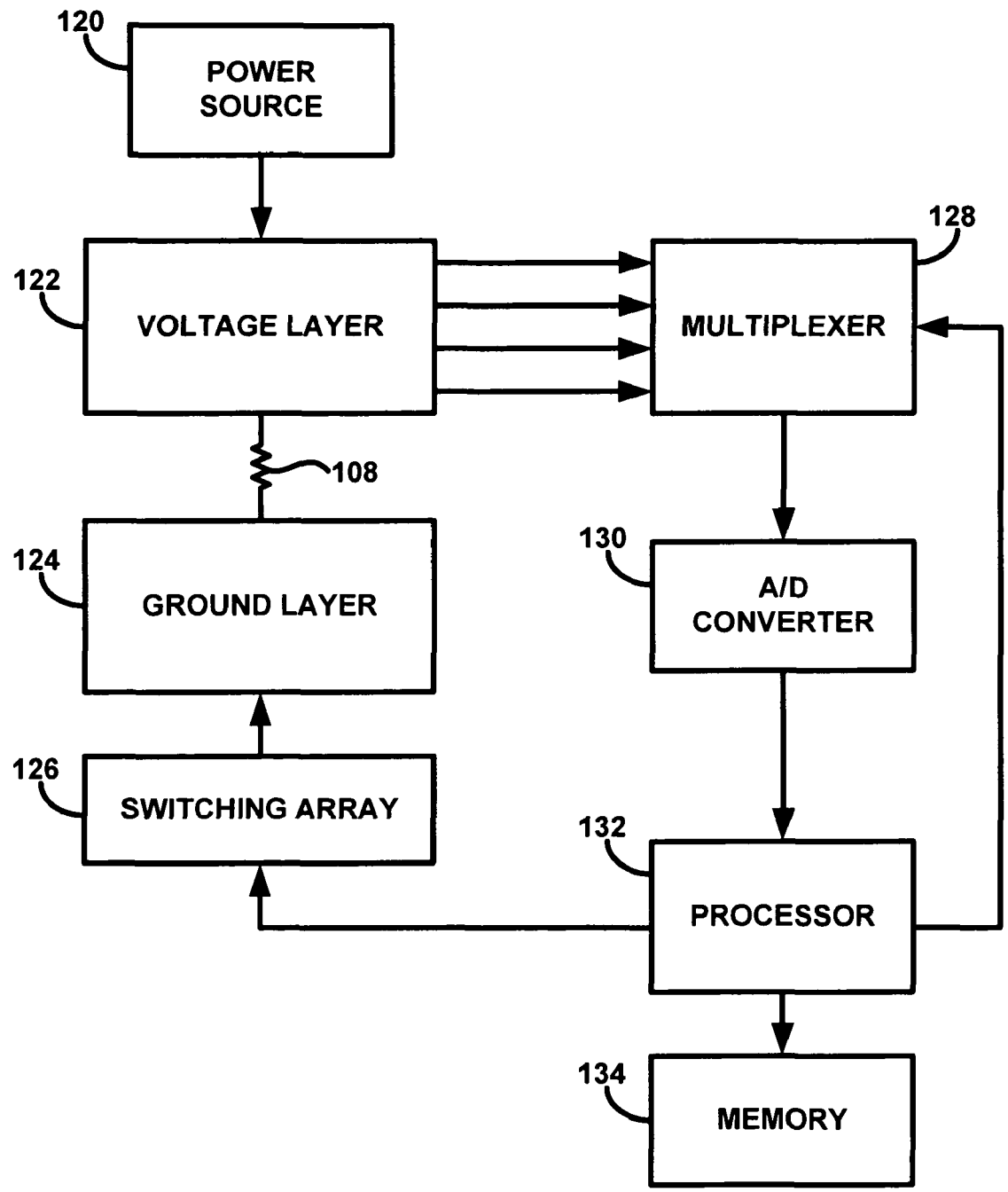
FIG. 9 is a functional block diagram illustrating the components of the addressable sensor array of FIG. 7.

FIG. 9 is a functional block diagram illustrating the components of the addressable sensor array of FIG. 8. As shown in FIG. 9, addressable sensor array 73 includes multiple components to measure and detect fluid voiding from patient 12. Power source 120 delivers voltage to voltage layer 122, i.e. first electrode layer 90, and a resistance 108 is measured between an electrode of the voltage layer and an electrode of ground layer 124, i.e., second electrode layer 92. Power source 120 may include a small, rechargeable or nonrechargeable battery. Switching array 126 closes one switch at a time to selectively isolate a portion of the electrodes of ground layer 124. Switching array 126 is controlled by processor 132.

A voltage from each electrode set isolated by the closed switch of the switching array is sent to multiplexer 128. Processor 132 manages multiplexer 128 to send one signal at a time through to analog to digital converter 130. Each digital signal is then delivered to processor 132, where the processor processes the signals and determines if a fluid is present based on the resistances measured. If a fluid is detected, processor 132 may use switching array 126 to scan through all electrode sets of voltage layer 122 and ground layer 124. Processor 132 processes each measured resistances and stored the voiding parameter in memory 134. Memory 134 may store the voiding parameters separately or tagged with a location and time as voiding information in a voiding log. Alternatively, processor 132 may continually operate switching array 126 to always scan the entire addressable sensor array 73 for fluid.

Figure 10:
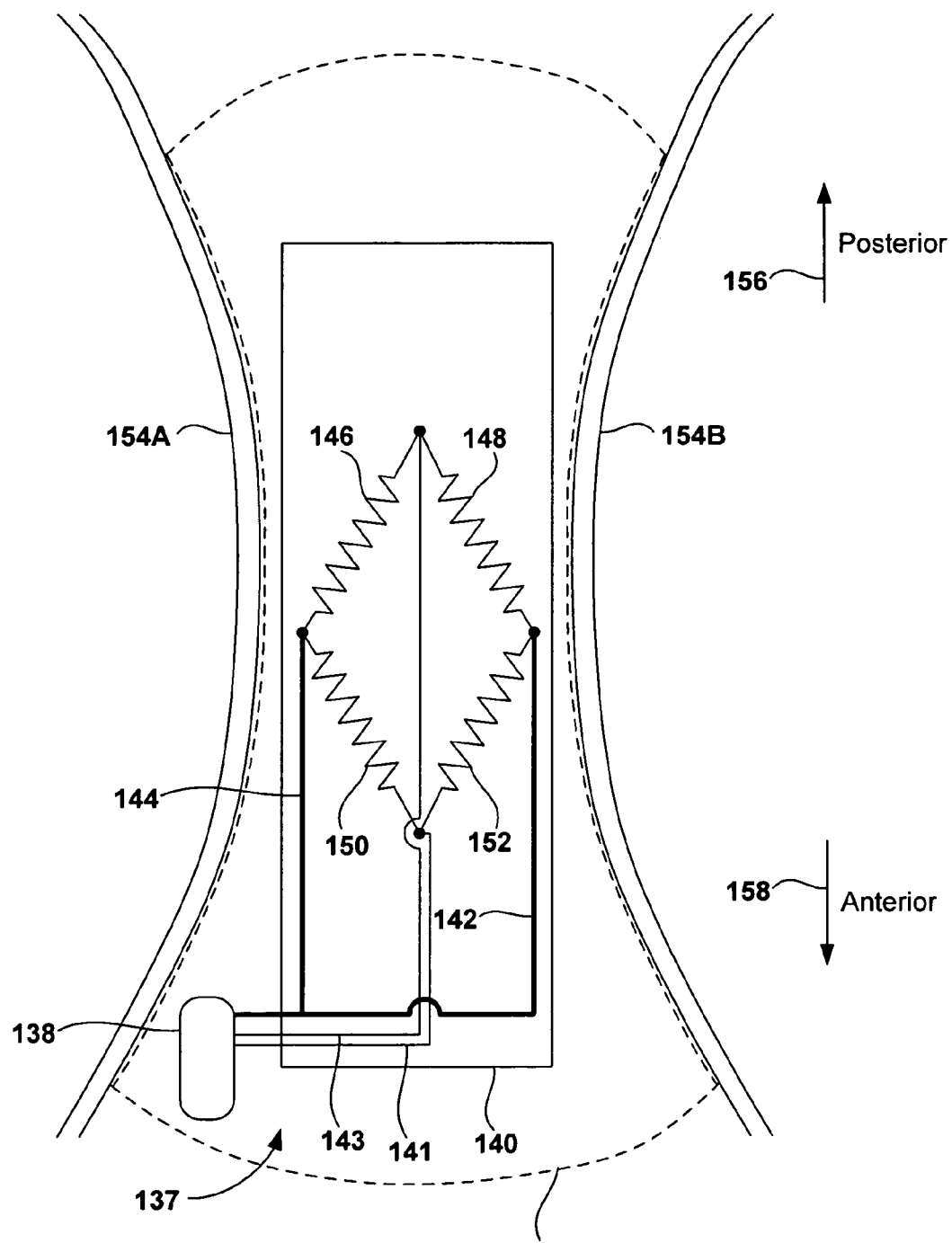
FIG. 10 is a schematic diagram illustrating an absorbent pad, incorporating a deformation sensor to detect voiding information.

FIG. 10 is a schematic diagram illustrating an absorbent pad 136, incorporating a deformation sensor 137 such as a strain gauge to detect a volume of urine voided by a patient. In general, deformation sensor 137 measures the strain exerted on pad 136 when urine is absorbed during a voiding event. Because deformation sensor 137 generates an output, i.e., an electrical signal, indicative of the strain exerted on pad 136, the signal may be processed to determine a volume of fluid absorbed by pad 136. Accordingly, deformation sensor 137 may transmit the signal to a master module or external device, such as master module 22 (FIG. 2) or external device 16 (FIGS. 1 and 2). The master module or external device may process the received signal to determine a volume of fluid absorbed by pad 136. Accordingly, a relationship between the strain exerted on pad 136 and the amount of fluid absorbed by pad 136 may be established. The relationship may be determined through experimentation and expressed in a mathematical equation in which the strain exerted on pad 136 is a function of the volume of fluid absorbed by pad 136.

Because deformation sensor 137 only measures strain exerted on pad 136, e.g., strain exerted through the thickness of pad 136, additional processing may be required to determine when the strain measured by deformation sensor 137 is a result of a voiding event or some other action by the patient, such as sitting, physical activity, or bowel incontinence. Using sitting as an example, the signal generated by deformation sensor 137 may be processed to determine a frequency of change in the signal because while the strain exerted on pad 136 may be increased when the patient is sitting, the increased strain exerted on pad 136 may increase suddenly corresponding to an impact event whereas increased strain resulting from a voiding event may occur over such a short period of time.

In addition, an increase in strain on pad 136 due to the patient sitting may be accompanied by a related decrease in strain when the patient moves from a sitting position. In contrast, a signal generated as a result of strain from a voiding event may be expected to have a relatively slower increase in value without a corresponding decrease. Further, the signal generated by deformation sensor 137 may be compared to a pre-defined threshold value to determine the cause of the strain because the strain exerted on pad 136 from the patient sitting may be substantially larger than the exerted on pad 136 as a result of a voiding event.

In some embodiments, other sensors may be used in combination with deformation sensor to determine if the strain measured by deformation sensor 137 is a result of a urinary voiding event or some other event. For example, detecting an increased strain on pad 136 without a corresponding increased in wetness of pad 136 may indicate bowel incontinence rather than a urinary voiding event. In any case, it is recognized that deformation sensor 137 may be used to detect strain on pad 136 and, correspondingly, determine an amount of fluid absorbed by pad 136, but additional processing may be required to determine when a change in strain on pad 136 is a result of a voiding event.

As shown in FIG. 10, deformation sensor 137 includes housing 138 coupled to resistive elements 146, 148, 150, and 152 configured to form a divided bridge circuit, e.g., a Wheatstone bridge. In the illustrated example, a voltage is applied across resistive elements 146, 148, 150, and 152 via wires 142 and 144 and a voltage is measured across wires 141 and 143. The voltage across wires 141 and 143 changes as a function of strain exerted on pad 136, i.e., as the pad swells upon absorption of urine voided by the patient. In particular, when strain is exerted on pad 136, the resistance of resistive elements 146, 148, 150, and 152 changes according to the magnitude of the force exerted on pad 136. As a result, a change in voltage across wires 142 and 144 may be measured and used to determine a volume of fluid absorbed by pad 136.

Housing 138 may include a circuit board and a power supply. The circuit board may include a telemetry circuit for transmitting the information to a master module or external device, such as master module 22 (FIG. 2) or external device 16 (FIGS. 1 and 2). In some embodiments, the circuit board may include a memory for storing the information and processing circuitry. The processing circuitry may determine if the strain is caused by a urinary voiding event or another activity by the patient. For example, the processing circuitry may compare the electrical signal to a pre-defined threshold to determine if the strain on pad 136 is a result of a urinary voiding event or as a result of the patient sitting.

In the illustrated example, deformation sensor 137 is incorporated in a layer 140 of pad 136. Accordingly, layer 140 may be referred to as a deformable sensor layer and may be located within, for example, an absorbent or middle layer of pad 136. Layer 140 may be interwoven with absorbent material of pad 136 or may be positioned between layers of absorbent material. In some embodiments, pad 136 may include multiple deformable sensors layers. In this case, each of the deformable sensor layers may be constructed and operate similar to deformable sensor 137 within layer 140, as described in FIG. 10. Multiple deformable sensor layers may provide more accurate and reliable measurements than a single deformable sensor.

Generally, pad 136 may be constructed similar to pad 20, i.e., with a transport layer for reducing wetness against the skin of the patient, a middle layer including absorbent material and sensors, and a bottom layer that acts as a barrier to prevent fluid absorbed by the pad from leaking out of the pad. In the illustrated example, pad 136 is shown as it may be positioned between undergarment 18 and skin of a patient. Undergarment 18 includes elastic bands 154A and 154B (collectively 'elastic bands 154') which help to retain any voided urine from leaking out from the sides of undergarment 18. Again, pad 136 is shaped to catch and retain any urine that is voided from a patient.

Deformation sensor 137 is merely exemplary and should not be considered limiting of the invention as broadly described in this disclosure. Rather, deformation sensor 137 provides an example configuration that is used to describe the operation of a deformation sensor within an absorbent pad for measuring urinary voiding parameters as described in this disclosure. The scope of the invention includes other types or configurations of deformable sensors that may be used instead of or in combination with deformation sensor 137. Other types of deformation sensors include capacitive, inductive, mechanical, optical, piezoresistive, and semi-conductive deformation sensors and any other sensor that converts a force, pressure, strain, tension, weight, and other mechanical forces into a change in electrical resistance which can then be measured.

FIGS. 11 and 12 are schematic diagrams illustrating the layered construction of an absorbent pad for measuring urinary voiding parameters, such as absorbent pad 20, 82, and 136. As previously described with respect to FIG. 2, pads 20, 82, 136 may include three distinct layers. In FIG. 11, a first layer comprises transport layer 160, a second layer comprises absorbent layers 164, 168 and sensor layers 162, 166, and a third layer comprises backing layer 170.

Transport layer 160 abuts or is proximate to the skin of the patient and distributes urine leaked by the patient over the surface of the pad. By distributing urine over the surface of the pad, the urine may be absorbed throughout the pad by absorbent layers 164, 168 of the middle layer to reduce wetness against the skin of the patient. In the illustrated example of FIG. 12, the middle layer includes sensor layers 162, 166 positioned between absorbent layers 164, 168. Sensor layers 162, 166 may include any number and type of sensors as previously described. It may be particularly advantageous to position sensor layer 162 as shown, i.e., directly below (inferior to) transport layer 160.

By positioning sensor layer 162 in this manner, sensory layer 162 may be exposed to urine leaked by the patient with high probability. Thus, urine leaked by the patient may be distributed over the surface of the pad by transport layer 160 to expose the sensors of sensor layer 162 to the urine. Again, sensors within sensor layer 162 may be located in a sensor area that comprises a portion of the area of sensory layer 162. The sensor area may be located proximate to the urethra of the patient or another area of the pad that is likely to absorb urine leaked by the patient.

Fluid leaked through transport layer 160 and sensor layer 162 is absorbed by absorbent layer 164. When absorbent layer 164 becomes saturated with fluid, fluid may leak through sensor layer 166 and be absorbed by absorbent layer 168. Absorbent layers 164, 168 may comprise cotton, cellulose, a hydro-gel, or a hydrophilic material that retains urine and may enable the pad to retain an ounce of fluid or greater than 20 ounces of fluid, depending on the material used to construct the pad and the size of the pad. Absorbent layers 164, 168 may allow a fluid to only be absorbed in an inferior direction, i.e., away from the patient. Consequently, when a fluid has been absorbed to a particular depth, the fluid is prevented from being re-absorbed in a superior direction, i.e., towards the patient.

Backing layer 170 prevents fluid that is not absorbed by absorbent layers 164, 168 from leaking out of the pad. In general, a pad may include any number of sensor layers and absorbent layers arranged in any order. For example, instead of alternating sensor and absorbent layers as shown in FIG. 11, multiple sensor layers may be positioned between absorbent layers.

FIG. 12 illustrates a pad, such as pad 20, 82, 136, comprising a transport layer 172, a middle layer including absorbent/sensor layers 174, 176, 178, and 180, and a back layer 182. Transport layer 160 and backing layer 182 perform the same functions as transport layer 160 and backing layer 170 of FIG. 11. However, in contrast to FIG. 11, FIG. 12 illustrates a pad with a middle layer in which the sensors are interwoven with the absorbent material. In particular, the middle layer includes absorbent/sensor layers 174, 176, 178, and 180. Each of absorbent/sensor layers 174, 176, 178, and 180 may include any number and type of sensors. For example, each of absorbent/sensor layers 174, 176, 178, and 180 may include various types of sensors or may include a single type of sensor. In any case, the sensors in each of absorbent/sensor layers 174, 176, 178, and 180 may be exposed to a fluid as it is absorbed through each layer. In this manner, the depth of absorption within the sensor pad may be used to estimate voiding volume. Absorbent/sensor layers 174, 176, 178, and 180 may be constructed of similar materials as absorbent layers 164, 168 of FIG. 11.

The construction of a particular pad may depend on a tradeoff between cost and performance. For example, a pad with the layered construction illustrated in FIG. 12 may cost more to manufacture and have improved performance in comparison to a pad with the layered construction illustrated in FIG. 11. Consequently, the construction of a pad may be determined by one or more economic variables.

Figure 13:
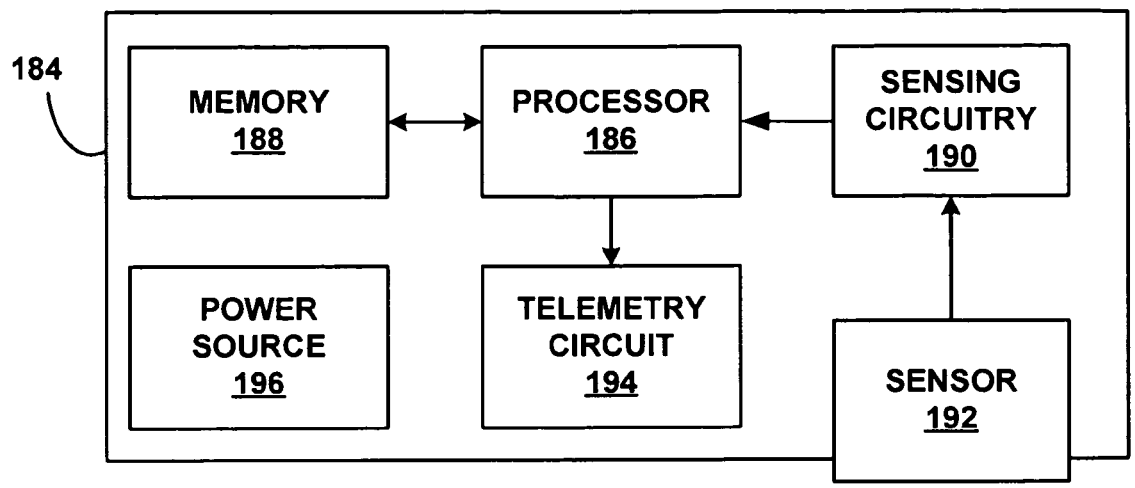
FIG. 13 is a functional block diagram illustrating various components of an exemplary sensor.

FIG. 13 is a functional block diagram illustrating various components of an exemplary sensor. As shown in FIG. 13, sensor 184 is an embodiment of sensors 24, 74 and 137, described herein as sensor 184. Sensor 184 may still be as described previously with respect to each sensor. In the example of FIG. 13, sensor 184 includes a processor 186, memory 188, sensing circuitry 190, telemetry circuit 194, power source 196 and sensor 192. Sensing circuitry 190 may be carried on a circuit board, along with processor 186, memory 188 and telemetry circuit 194. Sensor 184 may be referred to as a master module in alternative embodiments.

Sensor 184 may be any sensor such as a pressure sensor, impedance sensor, wetness sensor, pH sensor, deformation sensor, or any other sensor that transforms mechanical, chemical or electrical conditions into electrical signals representative of voiding information. Sensor 184 may also be coupled to an addressable sensor array or a deformable sensor layer, as described herein. The electrical signals may be amplified, filtered, and otherwise processed as appropriate by sensing circuitry 190 within sensor 184. In some embodiments, the signals may be converted to digital values and processed by processor 186 before being saved to memory 188 in the voiding log or sent to external device 16 via telemetry circuit 194.

Memory 188 stores instructions for execution by processor 186 and voiding information detected by sensing circuitry 190. Voiding information in the voiding log may then be sent to external device 16 for long-term storage and retrieval by a user. Memory 188 may include separate memories for storing instructions and voiding information. In some embodiments, processor 186 and memory 188 may implement loop recorder functionality in which processor 186 overwrites the oldest contents within the voiding log of the memory with new voiding information as storage limits are met, thereby conserving data storage resources within sensor 184. Alternatively, sensor 184 may be configured to immediately transmit measured voiding parameters or the generated voiding information to another device such as external device 16, in which case memory, processing overhead, and power consumption in sensor 184 can be substantially reduced.

Processor 186 controls telemetry circuit 194 to send voiding information to external device 16 on a continuous basis, at periodic intervals, or upon request from the device. The voiding information may be a pre-processed indication of a voiding event, in the case that sensor 184 includes the processing intelligence to analyze the sensed signals for voiding information. Alternatively, the voiding information may be raw sensor data obtained by sensor 184. In this case external device 16 may provide the processing intelligence to analyze the signals to populate the voiding log with voiding information. Wireless telemetry may be accomplished by radio frequency (RF) communication or proximal inductive interaction of sensor 184 with external device 16. In addition, wireless telemetry may follow Bluetooth protocols.

Power source 196 delivers operating power to the components of sensor 184. Power source 196 may include a small rechargeable or non-rechargeable battery and a power generation circuit to produce the operating power. Recharging may be accomplished through proximal inductive interaction between an external charger and an inductive charging coil within sensor 184. In some embodiments, power requirements may be small enough to allow sensor 184 to utilize patient motion and implement a kinetic energy-scavenging device to trickle charge a rechargeable battery. In other embodiments, traditional batteries may be used for a limited period of time.

In some embodiments, more complex characteristics may be used to detect voiding information from the measured voiding parameters such as deviation of a signal from an amplitude or frequency range, e.g., exceeding an upper threshold or falling below a lower threshold. Appropriate filter and amplifier circuitry, analog or digital, may be provided in the sensor or the processor to condition the signal so that such signal characteristics can be more specifically presented or isolated from extraneous information.

To detect voiding information, sensing circuit 190 may determine whether the signal output by sensor 192, or measured parameters, matches its requirements for voiding information. The signal output need not exactly match the corresponding requirements. Instead, a margin or difference threshold may be applied to indicate a voiding information if the sensor signal is within a given margin of the requirements. Again, the voiding information detection may be as simple as comparing sensor 192 signals to a threshold, e.g., to detect wetness. In more complex implementations, more detailed analysis of frequency and amplitude characteristics may be necessary to determine whether the sensor signal is sufficiently close to the requirements to define the output as voiding information.

As one example, processor 186 may generate a template signal corresponding a voiding event and apply a correlation technique. In some embodiments, a single sensor signal may be correlated with not just one, but multiple signal features, such as amplitude, frequency, time intervals, and the like. In addition, correlation values for the individual signal features may be weighted with coefficients to prioritize some features over other features. The correlation values for the individual features may be summed to produce an overall correlation value, which may be compared to a threshold value to detect the voiding information.

Using a digital signal processor (DSP), for example, the processor captures a series of samples of sensor 192 output. For example, the samples may be captured continuously, but an average is taken over a certain number of samples. If the average of the sample signals satisfies the output requirements, then the voiding information is detected.

Figure 14:
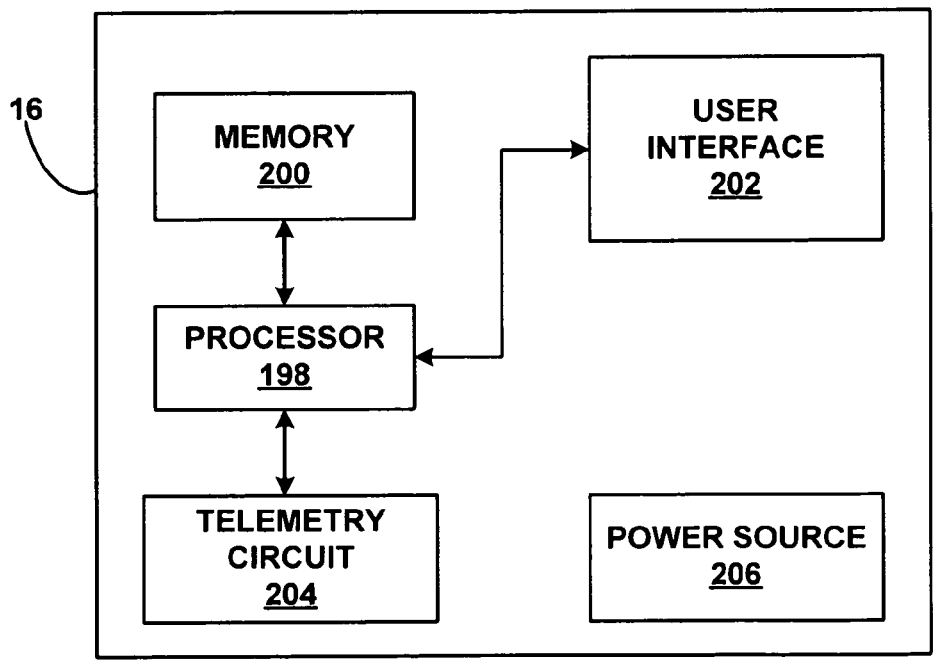
FIG. 14 is a functional block diagram illustrating various components of an external device that communicates wirelessly with a sensor.

FIG. 14 is a functional block diagram illustrating various components of an external device that communicates wirelessly with a sensor. As shown in FIG. 14, external device 16 includes processor 198, memory 200, telemetry circuit 204, user interface 202, and power source 206. The clinician or patient 12 interacts with user interface 202 in order to review the voiding log, modify a component of the voiding log, request voiding information from sensors 24, 74 or 137, or manually adjust one or more stimulation parameters of the stimulation therapy.

User interface 202 may include a screen and one or more input buttons that allow external device 16 to receive input from a user. The screen may be a liquid crystal display (LCD) or touch screen. The input buttons may include a touch pad, increase and decrease buttons, emergency shut off button, and other buttons needed to control the stimulation therapy. The clinician and patient 12 may review the voiding log of voiding information to determine an effective treatment or adjust currently delivered stimulation therapy.

Processor 198 controls user interface 202, retrieves data from memory 200 and stores data, such as voiding information, within the memory. Processor 198 also controls the transmission of voiding information through telemetry circuit 204 to sensors 24, 74 or 137. In some embodiments, telemetry circuit 204 may communicate with a stimulator as described in FIG. 17. Memory 200 includes operation instructions for processor 198 and voiding information in a voiding log. In embodiments, where stimulation therapy is also delivered, memory 200 may also store stimulation parameters to define the therapy. Memory 200 may also include a history of all user inputs and changes to the voiding information for later review if necessary.

Telemetry circuit 204 allows the transfer of data to and from sensors 24, 74 or 137. Telemetry circuit 204 may receive voiding information automatically from sensors 24, 74 or 137 as one of the sensors detects voiding information, at a scheduled time, or when the telemetry circuit detects the proximity of one of the sensors. Alternatively, telemetry circuit 204 may communicate with sensors 24, 74 or 137 when requested by a user through user interface 202. Power source 206 may be a rechargeable battery, such as a lithium ion or nickel metal hydride battery. Other rechargeable or conventional, nonrechargeable batteries may also be used. In some cases, external device 16 may be used when coupled to an alternating current outlet.

Figure 15:
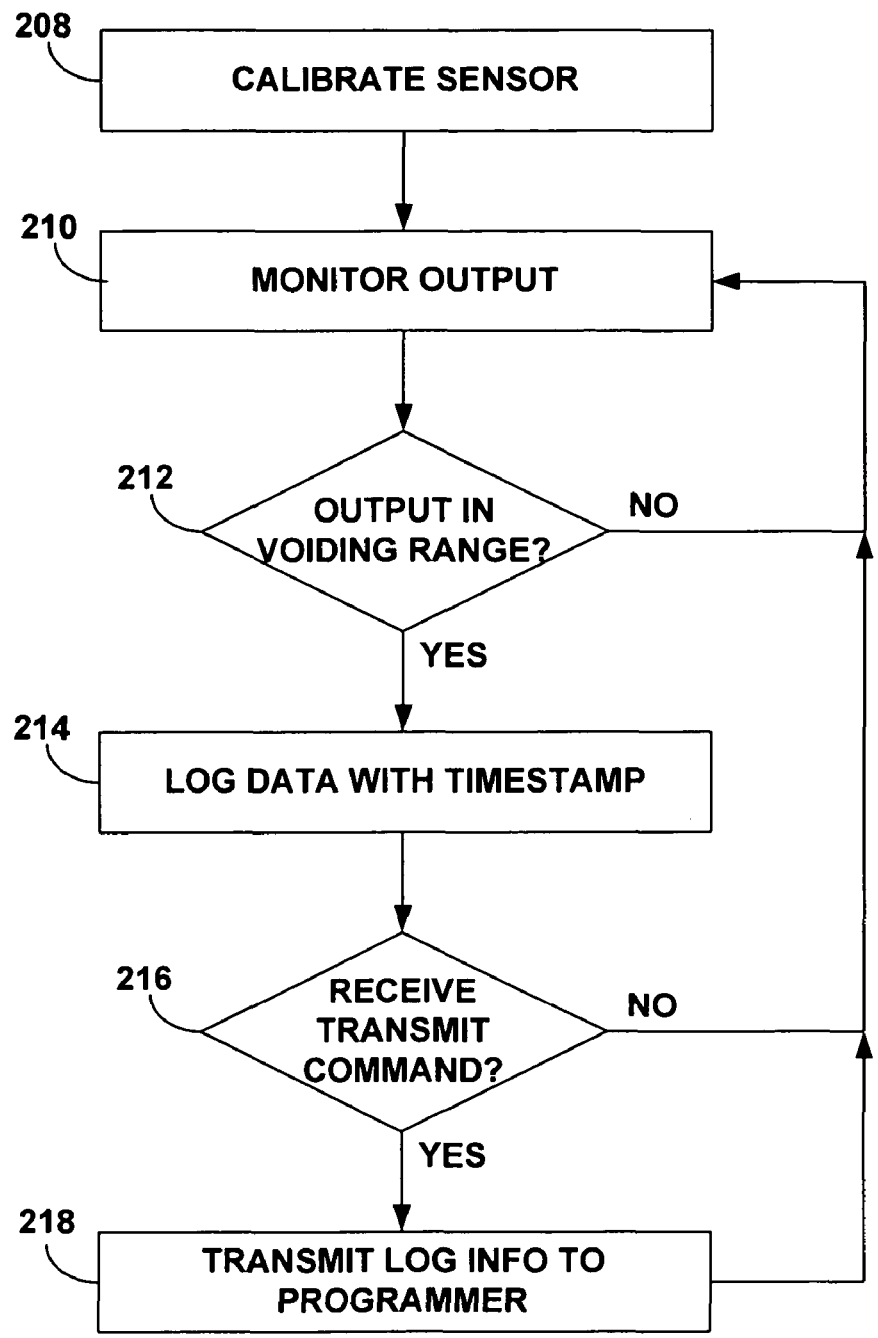
FIG. 15 is a flow chart illustrating a technique for detecting and storing voiding information from one sensor, and transmitting a voiding log to an external device when connected to the sensor.

FIG. 15 is a flow chart illustrating a technique for detecting and storing voiding information from one sensor, and transmitting a voiding log to an external device when connected to the sensor. As shown in FIG. 15, sensor 24 is used as an exemplary sensor to detect voiding information, but other sensors may be used. The detection begins by initially calibrating sensor 24 according to the non-voiding environment (208). Sensor 24 continually monitors the output of sensing element 44 to measure a voiding parameter and detect any new voiding information from patient 12 (210). If sensor 24 determines that output is not within a pre-determined voiding range (212), sensor 24 continues to monitor the output (210).

If the output is within the voiding range (212), sensor 24 stores the output as voiding information in the voiding log and timestamps the information (214). If sensor 24 has not received a transmit command from external device 16 (216), sensor 24 continues to monitor the output (210). If sensor 24 has received a transmit command from device 16 (216), sensor 24 transmits the voiding log to the programmer (218). Sensor 24 subsequently monitors the output once more (210).

In some embodiments, sensor 24 may store all output from sensing element 44 as voiding information in the voiding log. In this case, the memory of sensor 24 may be capable of storing a large quantity of voiding information. The clinician may desire to review all data, e.g. measured voiding parameters, generated by sensor 24, not just voiding information as determined by the sensor. All the data may be reviewed in its entirety by the clinician on external device 16. Alternatively, the clinician may process the data offline at external device 16 according to an arbitrary threshold to indicate which voiding information is indicative of a voiding event.

Figure 16:
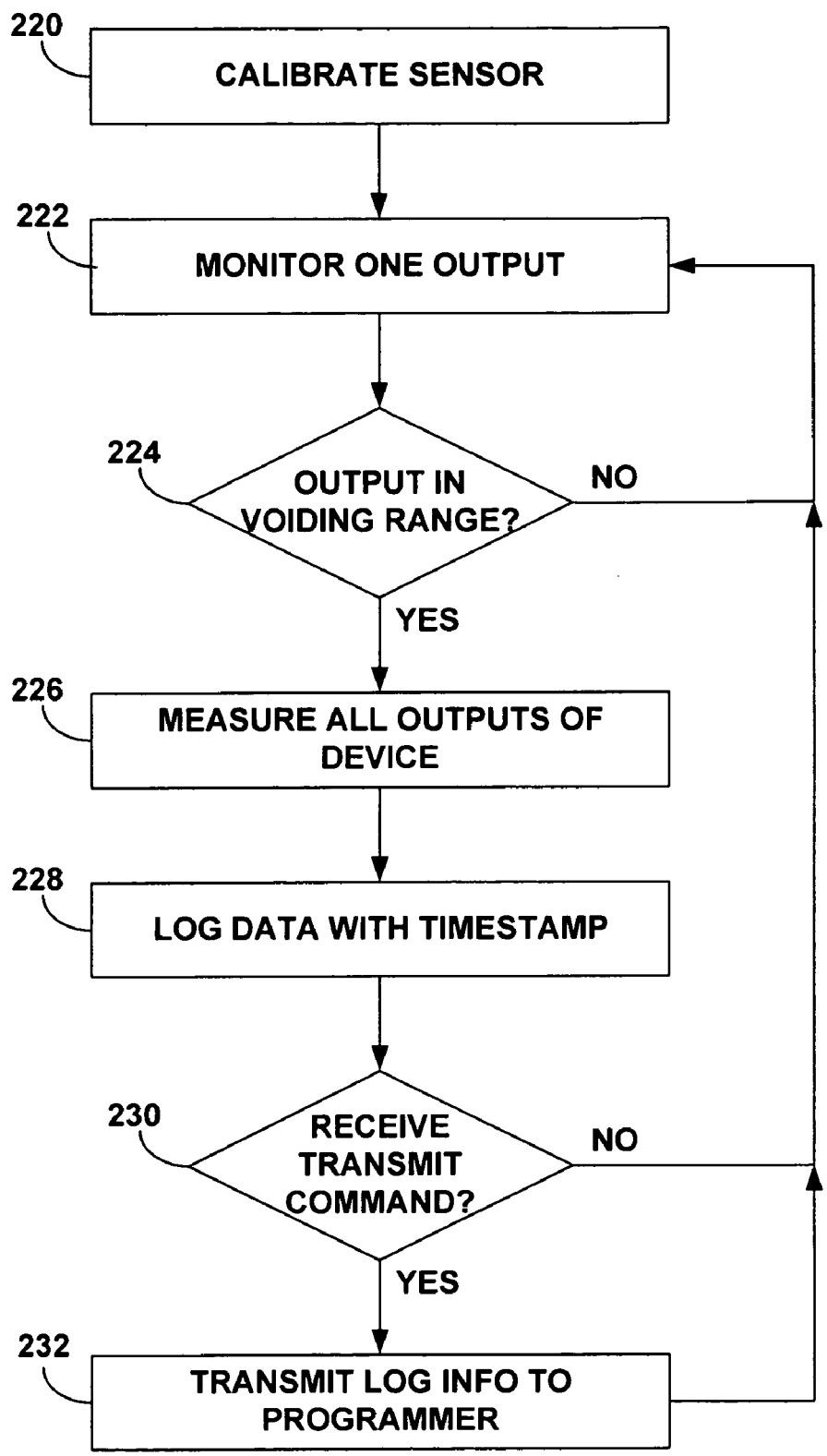
FIG. 16 is a flow chart illustrating a technique for detecting and storing voiding information from multiple sensors, and transmitting a voiding log to an external device when connected to the sensor.

FIG. 16 is a flow chart illustrating a technique for detecting and storing voiding information from multiple sensors, and transmitting a voiding log to an external device when connected to the sensor. As shown in FIG. 16, sensors 24 is used as an exemplary sensor to detect voiding information, but other sensors, e.g. sensors 74 and 137, may be used. At least one of the sensors 24 may be used to monitor fluid and direct the operation of other sensors. The detection begins by initially calibrating sensor 24 according to the non-voiding environment (220). At this time, all sensors 24 may be calibrated.

Sensor 24 continually monitors the output of sensing element 44 to measure a voiding parameter and detect any new voiding information from patient 12 (222). If sensor 24 determines that output is not within a pre-determined voiding range (224), sensor 24 continues to monitor the output (222). In the embodiment of sensor 74, one portion of the addressable sensor array may measure a voiding parameter and the sensor may monitor this output. Alternatively, sensor 74 may rotate through multiple portions of the addressable sensor array and monitor the output.

If the output is within the voiding range (224), sensor 24 signals the measurement of voiding parameters from all sensors (226). Sensor 24 stores the output as voiding information in the voiding log and timestamps the information (228). If sensor 24 has not received a transmit command from external device 16 (230), sensor 24 continues to monitor the output (222). If sensor 24 has received a transmit command from device 16 (230), sensor 24 transmits the voiding log to the programmer (232). Sensor 24 subsequently monitors the output once more (222).

In some embodiments, sensor 24 may store all output from sensing element 44 and all other sensors within absorbable pad 20 as voiding information in the voiding log. In this case, the memory of sensor 24 may be capable of storing a large quantity of voiding information. The clinician may desire to review all data, e.g. measured voiding parameters, generated by sensor 24, not just voiding information as determined by the sensor. All the data may be reviewed in its entirety by the clinician on external device 16. Alternatively, the clinician may process the data offline at external device 16 according to an arbitrary threshold to indicate which voiding information is indicative of a voiding event.

FIG. 17 is a schematic diagram illustrating a stimulation feedback system, incorporating an implanted stimulator that delivers stimulation therapy based upon voiding information from an absorbent pad. As shown in FIG. 17, system 234 includes undergarment 238, absorbent pad 240, stimulator 242, lead 244, and external programmer 246. Stimulator 242 delivers electrical stimulation therapy to a tissue of patient 12 via lead 244.

External programmer 246 communicates with one or more sensors, e.g., sensors 24, 74, or 137, of absorbable pad 240. In addition, external programmer 246 communicates with stimulator 242 to adjust one or more stimulation parameters of the stimulation therapy. External programmer 246 may be similar to external device 16, with the added capability of stimulation therapy adjustment. Stimulation parameters may include an electrode configuration, a pulse width, a pulse rate, a current amplitude, a voltage amplitude, or any other parameter that defines the electrical pulses.

Absorbent pad 240 may be any embodiment of absorbent pad 20 described herein. Absorbent pad 240 may also include any sensors 24, 74, and 137 that include discrete sensors, an addressable sensor array, and deformable sensor layer, described herein. The measured voiding parameters generate voiding information that is detected from absorbent pad 240 that is held in place by undergarment 238. The voiding information is transmitted to external programmer 246 and used by the programmer as closed loop feedback to adjust stimulation parameters for effective therapy. A clinician or patient 12 may view the voiding information in the voiding log and manually adjust one or more stimulation parameter. Alternatively, a processor of external programmer 246 may automatically process the voiding log to create automatic adjustments to the stimulation parameters to maintain effective therapy. In other embodiments, stimulator 242 communicates directly with absorbent pad 240, and the stimulator directly adjusts stimulation according to the voiding information.

Stimulator 242 may include a processor, memory, stimulation pulse generator, telemetry circuitry, and power source. Electrical pulses generated by the stimulation pulse generator are delivered to a tissue of patient 12 by lead 244, and one or more electrodes at a distal end of the lead transfer the electrical pulses to the tissue. The tissue may be any tissue that, when stimulated, aids in reducing urinary incontinence events of patient 12. These tissues may include a pudendal nerve, a sacral nerve, a nerve or nerves of the sacral plexus, or any other nerve of the pelvic floor. Other tissues may include muscles of the pelvic floor or the urinary sphincter. If the voiding information indicates that urine is or has been leaking from bladder 14, stimulator 242 may adjust one or more stimulation parameters to prevent the voiding events from occurring.

An exemplary range of electrical stimulation pulse parameters likely to be effective in treating incontinence, e.g., when applied to the sacral or pudendal nerves, are as follows:

1. Frequency: between approximately 0.5 Hz and 500 Hz, more preferably between approximately 5 Hz and 250 Hz, and still more preferably between approximately 10 Hz and 50 Hz.

2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage is delivered.

3. Pulse Width: between about 10 microseconds and 5000 microseconds, more preferably between approximately 100 microseconds and 1000 microseconds, and still more preferably between approximately 180 microseconds and 450 microseconds.

In some embodiments, patient 12 may wear absorbable pad 240 only when fine tuning of the stimulation parameters is desired. For example, patient 12 may wear absorbable pad 240 under undergarment 238 to create initial stimulation parameters and adjust the parameters until an optical treatment program is created. Alternatively, patient 12 may use absorbent pad 240 after current stimulation therapy is no longer efficacious. In this case, absorbent pad 240 may allow the clinician or stimulator 242 to adjust the current stimulation parameters until the absorbent pad no longer detects voiding events.

As mentioned previously absorbent pad 240 may be disposable or reusable by patient 12. If disposable, absorbent pad 240 may be discarded once urine or other bodily fluid comes into contact with the pad. If reusable, patient 12 may wash and disinfect absorbent pad 240 before using the pad another time. The sensors of absorbent pad 240 may be waterproof and resistant to corrosion.

Figure 18:
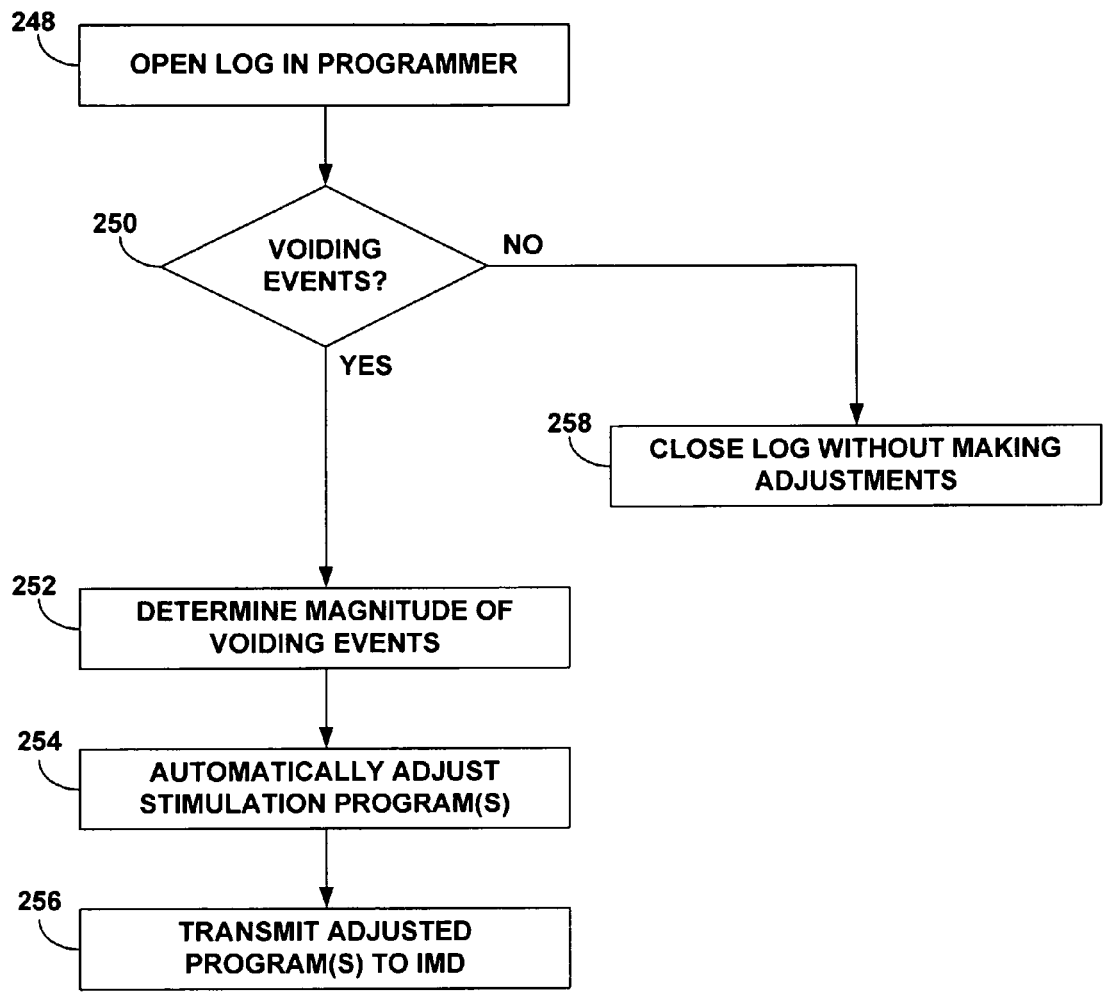
FIG. 18 is a flow chart illustrating a technique for automatically adjusting stimulation therapy with the voiding information from the absorbent pad.

FIG. 18 is a flow chart illustrating a technique for automatically adjusting stimulation therapy with the voiding information from the absorbent pad. As shown in FIG. 18, external programmer 246 begins the automatic adjustment process by opening the voiding log in the programmer (248). Programmer 246 processes the voiding log and identifies any voiding events from the measured voiding parameters such as volume (250). If programmer 246 does not identify any voiding events, there is no feedback to make stimulation adjustments, and the programmer closes the voiding log without modifying a single stimulation parameter of the therapy (258).

If programmer 246 identifies any voiding events in the voiding information, the programmer determines the magnitude of the voiding events (252). The magnitude of a voiding event may be the duration of the event, the frequency of leakage (i.e., number of leakage events per unit time such as day, week or month), the volume of urine voided, and/or other information characterizing the voiding event based upon one or more measured voiding parameters.

Programmer 246 uses the voiding information to automatically adjust one or more stimulation parameters, such as amplitude, pulse width or pulse rate, of one or more stimulation programs that were used to deliver therapy during the voiding event (254). The automatic adjustment may be governed by a set of rules or instruction of a memory within programmer 246. External programmer 246 subsequently transmits the one or more adjusted programs to stimulator 242, e.g. an implantable medical device (IMD), for improved stimulation therapy.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure Many embodiments of the invention have been described. Various modifications may be made without departing from the scope of the claims. For example, although the invention has been generally described in conjunction with integral sensors of an absorbent pad, sensors located elsewhere on patient 12 may be used in conjunction within an external programmer or even an implanted stimulator. In addition, other implantable medical devices, such as electrical muscle stimulation devices, functional electrical stimulation (FES) devices, and implantable drug delivery devices, each of which may be configured to treat incontinence or other conditions or disorders, may be used. These and other embodiments are within the scope of the following claims.

This invention claimed is:

1. A system comprising:
   an absorbent pad for placement adjacent to a patient;
   one or more sensors integrally formed with the absorbent pad and positioned to measure one or more voiding parameters;
   an implantable stimulator that delivers electrical stimulation therapy to the patient; and
   a processor that adjusts at least one stimulation parameter of the electrical stimulation therapy based on at least one voiding parameter measured by at least one of the sensors.

2. The system of claim 1, further comprising a memory that stores voiding information in a voiding log, wherein the voiding information comprises the one or more voiding parameters.

3. The system of claim 2, further comprising an external device that communicates with a telemetry circuit associated with the one or more sensors within the absorbent pad.

4. The system of claim 3, wherein the processor comprises a first processor, the system further comprising a master module that houses the memory and the telemetry circuitry, wherein the master module further comprises a second processor to perform processing operations associated with the one or more sensors.

5. The system of claim 2, wherein the processor detects a physiological event based on the measured voiding parameters and generates the voiding information.

6. The system of claim 1, wherein the one or more sensors are positioned in a sensor layer, and wherein the sensor layer is a two-dimensional array of sensors.

7. The system of claim 6, wherein at least a first sensor layer and a second sensor layer comprise a three-dimensional array of sensors.

8. The system of claim 7, wherein the one or more sensors of the first sensor layer measure a first voiding parameter and the one or more sensors of the second sensor layer measure a second voiding parameter.

9. The system of claim 1, wherein the one or more sensors are arranged in an addressable sensor array.

10. The system of claim 9, wherein the addressable sensor array comprises a first electrode group and a second electrode group, and the sensor detects resistance between the sets of electrodes in the first and second electrode groups to detect wetness.

11. The system of claim 1, wherein the one or more sensors include a deformation sensor that detects deformation of the pad to detect one or more voiding parameters.

12. The system of claim 1, wherein the absorbent pad comprises:
a transport layer that transports fluid away from the patient;
a middle layer that absorbs the fluid; and
a barrier layer that prevents the fluid from leaving the absorbent pad.

13. The system of claim 12, wherein the middle layer comprises one or more absorbent layers that absorb the fluid and one or more sensor layers that comprise one or more sensors integrally formed within the one or more sensor layers, and wherein the one or more sensor layers are separated by at least one of the one or more absorbent layers.

14. The system of claim 13, wherein the one or more absorbent layers selectively transport the fluid to at least one of the one or more sensors.

15. The system of claim 1, wherein the voiding parameters comprise at least one of a timestamp, a voiding event, a posture, an activity, a volume of fluid, a frequency of voiding events, or a urine component.

16. The system of claim 15, wherein the urine component comprises at least one of a hormone, an acidity, a bacteria, bilirubin, an impurity, glucose, metabolic acid, a nitrate, a protein, a blood element, or a puss.

17. The system of claim 1, wherein the one or more sensors measure at least one of an impedance, a strain, a temperature, a pH, or a chemical.

18. A method comprising:
sensing one or more voiding parameters via one or more sensors integrally formed within an absorbent pad disposed adjacent to a patient;
storing the one or more voiding parameters in a voiding log as voiding information; and
adjusting an electrical stimulation parameter of an implantable stimulator based on the voiding information.

19. The method of claim 18, wherein the absorbent pad is disposed between a portion of skin of the patient and an undergarment worn by the patient.

20. The method of claim 18, further comprising transmitting the voiding log to an external device via a telemetry circuit associated with the one or more sensors within the absorbent pad.

21. The method of claim 18, further comprising performing processing operations associated with the one or more sensors within a master module of the absorbent pad.

22. The method of claim 18, wherein measuring one or more voiding parameters comprises measuring the one or more voiding parameters via a two dimensional array of the one or more sensors as a sensor layer.

23. The method of claim 22, wherein measuring one or more voiding parameters comprises measuring the one or more voiding parameters via a three dimensional array of the two or more sensor layers.

24. The method of claim 23, wherein the one or more sensors of the first sensor layer measure a first voiding parameter and the one or more sensors of the second sensor layer measure a second voiding parameter.

25. The method of claim 18, further comprising transmitting the one or more voiding parameters from each of the one or more sensors to a master module of the absorbent pad.

26. The method of claim 18, wherein the addressable sensor array comprises a first electrode group and a second electrode group, wherein sensing includes sensing a resistance between the sets of electrodes in the first and second electrode groups to detect wetness.

27. The method of claim 18, wherein sensing includes sensing deformation of the pad to detect one or more voiding parameters.

28. The method of claim 18, further comprising:
transporting a fluid away from the patient;
absorbing the fluid in the absorbent pad; and
preventing the fluid from leaving the absorbent pad.

29. The method of claim 18, wherein the voiding parameters comprise at least one of a timestamp, a voiding event, a posture, an activity, a volume of fluid, a frequency of voiding events, or a urine component.

30. The method of claim 29, wherein the urine component comprises at least one of a hormone, an acidity, a bacteria, bilirubin, an impurity, glucose, metabolic acid, a nitrate, a protein, a blood element, or a puss.

31. The method of claim 18, wherein sensing one or more voiding parameters comprises measuring at least one of an impedance, a strain, a temperature, a pH, or a chemical.

32. The system of claim 1, wherein the processor determines a disorder of the patient based on the parameters received from at least one of the sensors, the disorder comprising at least one of stress incontinence, urinary incontinence or nocturnal enuresis.

33. The system of claim 1, wherein at least one of the sensors detects wetness, the system further comprising a master module that determines whether the wetness is from urine.

34. The system of claim 1, wherein the processor determines a disorder of the patient based on the parameters received from at least one of the sensors, the disorder comprising at least one of stress incontinence, urinary incontinence or nocturnal enuresis.

35. The system of claim 1, wherein at least one of the sensors detects wetness, the system further comprising a master module that determines whether the wetness is from urine.

36. The system of claim 1, wherein at least one of the sensors generates a signal indicative of a posture of the patient.

37. The system of claim 3, wherein the external device comprises a user interface to receive modifications to the voiding log from a user.

38. The system of claim 1, wherein the at least one stimulation parameter comprises at least one of an electrode configuration, pulse rate, pulse width, voltage amplitude or current amplitude of the electrical stimulation therapy.

39. The system of claim 1, further comprising a memory that stores instructions that identify an electrical stimulation parameter to be adjusted by processor based on different types of voiding information generated from the voiding parameters.

40. The system of claim 10, wherein the sensor determines a volume of fluid absorbed by the absorbent pad based on a resistance between the first and second electrode groups.

41. The method of claim 18, wherein the electrical stimulation parameter comprises at least one of an electrode configuration, pulse rate, pulse width, voltage amplitude or current amplitude.

42. The method of claim 18, wherein sensing one or more voiding parameters comprises sensing a posture of a patient via at least one of the sensors integrally formed within the absorbent pad.

43. The method of claim 26, wherein the one or more sensors comprises an addressable sensor array comprising a first electrode group and a second electrode group, and sensing comprises measuring a resistance between the first and second electrode groups to determine a volume of fluid absorbed by the absorbent pad.

* * * * *

UNITED STATES PATENT AND TRADEMARK OFFICE
CERTIFICATE OF CORRECTION

| | | |
|---|---|---|
| PATENT NO. | : 7,855,653 B2 | Page 1 of 1 |
| APPLICATION NO. | : 11/414508 | |
| DATED | : December 21, 2010 | |
| INVENTOR(S) | : John C. Rondoni | |

It is certified that error appears in the above-identified patent and that said Letters Patent is hereby corrected as shown below:

<u>Column 27</u>

Claim 22 should correctly read -- The method of claim 18, wherein measuring one or more voiding parameters comprises measuring the one or more voiding parameters via a two dimensional array of the one or more sensors, wherein the two-dimensional array of sensors defines a sensor layer. --

Claim 23 should correctly read -- The method of claim 18, wherein measuring one or more voiding parameters comprises measuring the one or more voiding parameters via a three dimensional array of sensors, wherein the three-dimensional array of sensors comprises a first sensor layer and a second sensor layer, the first and second sensor layers each comprising one or more sensors. --

Signed and Sealed this
Fourteenth Day of June, 2011

David J. Kappos
*Director of the United States Patent and Trademark Office*

UNITED STATES PATENT AND TRADEMARK OFFICE
CERTIFICATE OF CORRECTION

PATENT NO. : 7,855,653 B2                                                                 Page 1 of 1
APPLICATION NO. : 11/414508
DATED : December 21, 2010
INVENTOR(S) : John C. Rondoni It is certified that error appears in the above-identified patent and that said Letters Patent is hereby corrected as shown below:

Column 27, lines 46-49,

Claim 22 should correctly read -- The method of claim 18, wherein measuring one or more voiding parameters comprises measuring the one or more voiding parameters via a two dimensional array of the one or more sensors, wherein the two-dimensional array of sensors defines a sensor layer. --

Column 27, lines 50-53,
Claim 23 should correctly read -- The method of claim 18, wherein measuring one or more voiding parameters comprises measuring the one or more voiding parameters via a three dimensional array of sensors, wherein the three-dimensional array of sensors comprises a first sensor layer and a second sensor layer, the first and second sensor layers each comprising one or more sensors. --

This certificate supersedes the Certificate of Correction issued June 14, 2011.

Signed and Sealed this
Twelfth Day of July, 2011

David J. Kappos
*Director of the United States Patent and Trademark Office*